United States Patent
Zemlok et al.

(10) Patent No.: US 9,055,943 B2
(45) Date of Patent: Jun. 16, 2015

(54) HAND HELD SURGICAL HANDLE ASSEMBLY, SURGICAL ADAPTERS FOR USE BETWEEN SURGICAL HANDLE ASSEMBLY AND SURGICAL END EFFECTORS, AND METHODS OF USE

(75) Inventors: Michael Zemlok, Prospect, CT (US); Ryan Williams, Milford, CT (US); Stanislaw Marczyk, Stratford, CT (US); Nihir Patel, Stamford, CT (US); David Chowaniec, Rocky Hill, CT (US)

(73) Assignee: Covidien LP, Mansfield, MA (US)

( * ) Notice: Subject to any disclaimer, the term of this patent is extended or adjusted under 35 U.S.C. 154(b) by 252 days.

(21) Appl. No.: 13/484,975

(22) Filed: May 31, 2012

(65) Prior Publication Data

US 2012/0253329 A1    Oct. 4, 2012

Related U.S. Application Data

(60) Continuation-in-part of application No. 13/331,047, filed on Dec. 20, 2011, now Pat. No. 8,968,276, which is a continuation-in-part of application No. 12/946,082, filed on Nov. 15, 2010, now Pat. No.

(Continued)

(51) Int. Cl.
*A61B 17/68*    (2006.01)
*A61B 17/072*   (2006.01)
*A61B 17/115*   (2006.01)
*A61B 17/00*    (2006.01)

(52) U.S. Cl.
CPC .............. *A61B 17/072* (2013.01); *A61B 17/115* (2013.01); *A61B 2017/0023* (2013.01); *A61B 2017/00371* (2013.01); *A61B 2017/00398* (2013.01); *A61B 2017/00464* (2013.01); *A61B 2017/00473* (2013.01)

(58) Field of Classification Search
CPC ............. A61B 2017/00398; A61B 2017/2923; A61B 2017/2912; A61B 2017/2932
USPC ............................................................ 606/1
See application file for complete search history.

(56) References Cited

U.S. PATENT DOCUMENTS

| 4,722,685 A | 2/1988 | de Estrada et al. |
| 4,823,807 A | 4/1989 | Russell et al. |

(Continued)

FOREIGN PATENT DOCUMENTS

| AU | 2008229795 A1 | 4/2009 |
| CA | 2451558 | 1/2003 |

(Continued)

OTHER PUBLICATIONS

Extended European Search Report corresponding to EP 13 17 5377.4, completed Jul. 30, 2013, and mailed Aug. 6, 2013; (5 pp).

(Continued)

*Primary Examiner* — Aaron Roane

(57) ABSTRACT

Adapter assemblies are provided for selectively interconnecting a surgical end effector that is configured to perform at least a pair of functions and a surgical device that is configured to actuate the end effector, wherein the end effector includes a first axially translatable drive member and a second axially translatable drive member, and wherein the surgical device includes a first rotatable drive shaft and a second rotatable drive shaft.

8 Claims, 26 Drawing Sheets

Related U.S. Application Data 8,806,973, said application No. 13/331,047 is a continuation-in-part of application No. 12/758,900, filed on Apr. 13, 2010, which is a continuation-in-part of application No. 12/622,827, filed on Nov. 20, 2009, said application No. 13/311,047 is a continuation-in-part of application No. 13/089,672, filed on Apr. 19, 2011, now Pat. No. 8,342,379, which is a division of application No. 12/235,362, filed on Sep. 22, 2008, now Pat. No. 7,963,433, said application No. 13/331,047 is a continuation-in-part of application No. 13/089,473, filed on Apr. 19, 2011, now Pat. No. 9,017,371, which is a division of application No. 12/235,362, filed on Sep. 22, 2008, now Pat. No. 7,963,433, said application No. 13/331,047 is a continuation-in-part of application No. 13/090,286, filed on Apr. 20, 2011, now Pat. No. 8,272,554, which is a division of application No. 12/235,362, filed on Sep. 22, 2008, now Pat. No. 7,963,433.

(60) Provisional application No. 61/308,045, filed on Feb. 25, 2010, provisional application No. 61/265,942, filed on Dec. 2, 2009, provisional application No. 60/974,267, filed on Sep. 21, 2007.

(56) References Cited

U.S. PATENT DOCUMENTS

| | | | |
|---|---|---|---|
| 5,301,061 A | 4/1994 | Nakada et al. | |
| 5,411,508 A | 5/1995 | Bessler et al. | |
| 5,427,087 A | 6/1995 | Ito et al. | |
| 5,540,375 A | 7/1996 | Bolanos et al. | |
| 5,540,706 A | 7/1996 | Aust et al. | |
| 5,632,432 A | 5/1997 | Schulze et al. | |
| 5,658,300 A | 8/1997 | Bito et al. | |
| 5,693,042 A | 12/1997 | Boiarski et al. | |
| 5,762,603 A | 6/1998 | Thompson | |
| 5,782,396 A | 7/1998 | Mastri et al. | |
| 6,010,054 A | 1/2000 | Johnson et al. | |
| 6,032,849 A | 3/2000 | Mastri et al. | |
| 6,126,651 A | 10/2000 | Mayer | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,371,909 B1 | 4/2002 | Hoeg et al. | |
| 6,459,822 B1 | 10/2002 | Hathaway et al. | |
| 6,471,637 B1 | 10/2002 | Green et al. | |
| 6,645,218 B1 | 11/2003 | Cassidy et al. | |
| 6,654,999 B2 | 12/2003 | Stoddard et al. | |
| 6,783,533 B2 | 8/2004 | Green et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,905,057 B2 | 6/2005 | Swayze et al. | |
| 6,986,451 B1 | 1/2006 | Mastri et al. | |
| 6,988,649 B2 | 1/2006 | Shelton, IV et al. | |
| RE39,152 E | 6/2006 | Aust et al. | |
| 7,059,508 B2 | 6/2006 | Shelton, IV et al. | |
| 7,122,029 B2 | 10/2006 | Koop et al. | |
| 7,140,528 B2 | 11/2006 | Shelton, IV | |
| 7,147,138 B2 | 12/2006 | Shelton | |
| 7,172,104 B2 * | 2/2007 | Scirica et al. | 227/175.2 |
| 7,225,964 B2 | 6/2007 | Mastri et al. | |
| 7,238,021 B1 | 7/2007 | Johnson | |
| 7,407,078 B2 | 8/2008 | Shelton, IV et al. | |
| 7,481,824 B2 | 1/2009 | Boudreaux et al. | |
| 7,565,993 B2 | 7/2009 | Milliman et al. | |
| 7,575,144 B2 | 8/2009 | Ortiz et al. | |
| 7,699,835 B2 | 4/2010 | Lee et al. | |
| 7,793,812 B2 | 9/2010 | Moore et al. | |
| 7,822,458 B2 | 10/2010 | Webster, III et al. | |
| 7,845,534 B2 | 12/2010 | Viola et al. | |
| 7,857,185 B2 | 12/2010 | Swayze et al. | |
| 7,870,989 B2 | 1/2011 | Viola et al. | |
| 7,922,719 B2 | 4/2011 | Ralph et al. | |
| 7,947,034 B2 | 5/2011 | Whitman | |
| 7,954,682 B2 | 6/2011 | Giordano et al. | |
| 7,959,051 B2 | 6/2011 | Smith et al. | |
| 7,967,179 B2 | 6/2011 | Olson et al. | |
| 8,016,178 B2 | 9/2011 | Olson et al. | |
| 8,025,199 B2 | 9/2011 | Whitman et al. | |
| 8,052,024 B2 | 11/2011 | Viola et al. | |
| 8,114,118 B2 | 2/2012 | Knodel et al. | |
| 8,132,705 B2 | 3/2012 | Viola et al. | |
| 8,152,516 B2 | 4/2012 | Harvey et al. | |
| 8,157,150 B2 | 4/2012 | Viola et al. | |
| 8,182,494 B1 | 5/2012 | Yencho et al. | |
| 8,186,587 B2 | 5/2012 | Zmood et al. | |
| 8,235,273 B2 | 8/2012 | Olson et al. | |
| 8,272,554 B2 | 9/2012 | Whitman et al. | |
| 8,292,150 B2 | 10/2012 | Bryant | |
| 8,342,379 B2 | 1/2013 | Whitman et al. | |
| 8,353,440 B2 | 1/2013 | Whitman et al. | |
| 8,365,633 B2 | 2/2013 | Simaan et al. | |
| 8,371,492 B2 | 2/2013 | Aranyi et al. | |
| 8,424,739 B2 | 4/2013 | Racenet et al. | |
| 8,454,585 B2 | 6/2013 | Whitman | |
| 8,505,802 B2 | 8/2013 | Viola et al. | |
| 8,517,241 B2 | 8/2013 | Nicholas et al. | |
| 8,551,076 B2 | 10/2013 | Duval et al. | |
| 8,561,871 B2 | 10/2013 | Rajappa et al. | |
| 8,623,000 B2 | 1/2014 | Humayun et al. | |
| 8,632,463 B2 | 1/2014 | Drinan et al. | |
| 8,647,258 B2 | 2/2014 | Aranyi et al. | |
| 8,657,174 B2 | 2/2014 | Yates et al. | |
| 8,696,552 B2 | 4/2014 | Whitman | |
| 8,708,213 B2 | 4/2014 | Shelton, IV et al. | |
| 8,806,973 B2 | 8/2014 | Ross et al. | |
| 8,851,355 B2 | 10/2014 | Aranyi et al. | |
| 8,858,571 B2 | 10/2014 | Shelton, IV et al. | |
| 2003/0038938 A1 | 2/2003 | Jung et al. | |
| 2003/0130677 A1 | 7/2003 | Whitman et al. | |
| 2004/0133189 A1 | 7/2004 | Sakurai | |
| 2004/0176751 A1 | 9/2004 | Weitzner et al. | |
| 2005/0125027 A1 | 6/2005 | Knodel et al. | |
| 2005/0131442 A1 | 6/2005 | Yachia et al. | |
| 2006/0278680 A1 | 12/2006 | Viola et al. | |
| 2007/0023477 A1 | 2/2007 | Whitman et al. | |
| 2007/0055219 A1 | 3/2007 | Whitman et al. | |
| 2007/0152014 A1 | 7/2007 | Gillum et al. | |
| 2007/0175961 A1 | 8/2007 | Shelton et al. | |
| 2008/0110958 A1 | 5/2008 | McKenna et al. | |
| 2008/0188841 A1 | 8/2008 | Tomasello et al. | |
| 2008/0197167 A1 | 8/2008 | Viola et al. | |
| 2008/0255413 A1 | 10/2008 | Zemlok et al. | |
| 2009/0090763 A1 | 4/2009 | Zemlok et al. | |
| 2009/0145947 A1 | 6/2009 | Scirica et al. | |
| 2009/0171147 A1 | 7/2009 | Lee et al. | |
| 2009/0179063 A1 | 7/2009 | Milliman et al. | |
| 2009/0254094 A1 | 10/2009 | Knapp et al. | |
| 2010/0069942 A1 | 3/2010 | Shelton, IV | |
| 2010/0225073 A1 | 9/2010 | Porter et al. | |
| 2011/0077673 A1 | 3/2011 | Grubac et al. | |
| 2011/0125138 A1 | 5/2011 | Malinouskas et al. | |
| 2011/0139851 A1 | 6/2011 | McCuen | |
| 2011/0155783 A1 | 6/2011 | Rajappa et al. | |
| 2011/0174099 A1 | 7/2011 | Ross et al. | |
| 2011/0204119 A1 | 8/2011 | McCuen | |
| 2011/0290854 A1 | 12/2011 | Timm et al. | |
| 2011/0295242 A1 | 12/2011 | Spivey et al. | |
| 2011/0295269 A1 | 12/2011 | Swensgard et al. | |
| 2012/0000962 A1 | 1/2012 | Racenet et al. | |
| 2012/0089131 A1 | 4/2012 | Zemlok et al. | |
| 2012/0143002 A1 | 6/2012 | Aranyi et al. | |
| 2012/0172924 A1 | 7/2012 | Allen, IV | |
| 2012/0223121 A1 | 9/2012 | Viola et al. | |
| 2012/0253329 A1 | 10/2012 | Zemlok et al. | |
| 2012/0310220 A1 | 12/2012 | Malkowski et al. | |
| 2012/0323226 A1 | 12/2012 | Chowaniec et al. | |
| 2013/0018361 A1 | 1/2013 | Bryant | |
| 2013/0098966 A1 | 4/2013 | Kostrzewski et al. | |
| 2013/0098968 A1 | 4/2013 | Aranyi et al. | |

(56) References Cited

U.S. PATENT DOCUMENTS

| | | |
|---|---|---|
| 2013/0098969 A1 | 4/2013 | Scirica et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2014/0110455 A1 | 4/2014 | Ingmanson et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |

FOREIGN PATENT DOCUMENTS

| | | |
|---|---|---|
| CN | 102 247 182 | 11/2011 |
| DE | 102008053842 A1 | 5/2010 |
| EP | 0634144 A1 * | 7/1994 |
| EP | 0 634 144 | 1/1995 |
| EP | 0 634 144 A1 | 1/1995 |
| EP | 0648476 A1 | 4/1995 |
| EP | 0686374 A2 | 12/1995 |
| EP | 0705571 A1 | 4/1996 |
| EP | 1723913 A1 | 11/2006 |
| EP | 1772105 A1 | 4/2007 |
| EP | 1813199 | 8/2007 |
| EP | 1813211 | 8/2007 |
| EP | 1943954 A2 | 7/2008 |
| EP | 1943956 A2 | 7/2008 |
| EP | 2 005 898 | 12/2008 |
| EP | 2 005 898 A2 | 12/2008 |
| EP | 2044890 A1 | 4/2009 |
| EP | 2 098 170 | 9/2009 |
| EP | 2 098 170 A2 | 9/2009 |
| EP | 2098170 A2 * | 9/2009 |
| EP | 2100562 A2 | 9/2009 |
| EP | 2165664 A2 | 3/2010 |
| EP | 2236098 | 10/2010 |
| EP | 2263568 | 12/2010 |
| EP | 2272443 A1 | 1/2011 |
| EP | 2316345 A1 | 5/2011 |
| EP | 2324776 A2 | 5/2011 |
| EP | 2329773 | 6/2011 |
| EP | 2333509 A1 | 6/2011 |
| EP | 2462878 A1 | 6/2012 |
| EP | 2462880 A2 | 6/2012 |
| EP | 2491872 A1 | 8/2012 |
| EP | 2586382 | 5/2013 |
| EP | 2606834 | 6/2013 |
| EP | 2676615 A2 | 12/2013 |
| ES | 2333509 A1 | 2/2010 |
| JP | 08-038488 | 2/1996 |
| JP | 2005-125075 A | 5/2005 |
| WO | 99/15086 A1 | 4/1999 |
| WO | WO 03/000138 | 1/2003 |
| WO | 03/030743 A2 | 4/2003 |
| WO | 03065916 A1 | 8/2003 |
| WO | 03090630 A2 | 11/2003 |
| WO | 2007016290 A2 | 2/2007 |
| WO | WO 2007/014355 | 2/2007 |
| WO | WO 2007/014355 A2 | 2/2007 |
| WO | 2007137304 A2 | 11/2007 |
| WO | WO 2009/039506 A1 | 3/2009 |
| WO | 2009/143092 A1 | 11/2009 |
| WO | 2009149234 A1 | 12/2009 |
| WO | WO 2011/108840 | 9/2011 |
| WO | 2012040984 A1 | 4/2012 |

OTHER PUBLICATIONS

European Search Report corresponding to European Application EP 10 25 2037.6; completed Mar. 1, 2011 and mailed Mar. 9, 2011; 3 pages.
European Search Report corresponding to European Application EP 13 17 5479.8, mailed on Oct. 10, 2013; 7 pages.
Extended European Search Report corresponding to EP No. 11 17 8021.9, mailed Jun. 4, 2013; (3 pp).
Extended European Search Report corresponding to EP No. 13 16 3033.7, completed Jun. 27, 2013 and mailed Jul. 15, 2013; (8 pp).
Extended European Search Report corresponding to EP No. 12 18 6177.7, completed Aug. 14, 2013 and mailed Aug. 23, 2013; (8 pp).
Partial European Search Report corresponding to EP No. 13 17 1742.3, completed Sep. 17, 2013 and mailed Sep. 25, 2013; (8 pp).
Partial European Search Report corresponding to EP No. 13 17 2400.7, completed Sep. 18, 2013 and mailed Oct. 1, 2013; (7 pp).
Extended European Search Report corresponding to EP No. 13 17 5475.6, completed Sep. 23, 2013 and mailed Oct. 1, 2013; (8 pp).
Extended European Search Report corresponding to EP No. 13 17 5478.0, completed Sep. 24, 2013 and mailed Oct. 2, 2013; (6 pp).
Extended European Search Report corresponding to EP No. 13 17 5479.8, completed Sep. 27, 2013 and mailed Oct. 10, 2013; (7 pp).
Partial Extended European Search Report corresponding to EP 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
Extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.

* cited by examiner

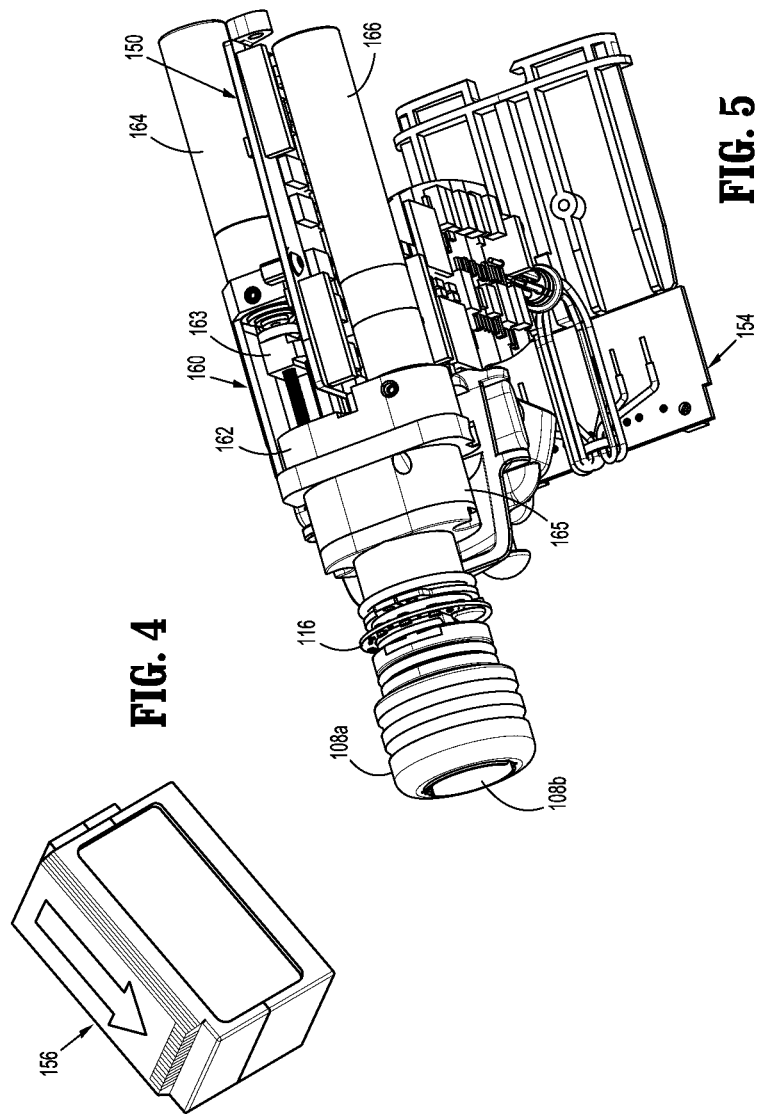

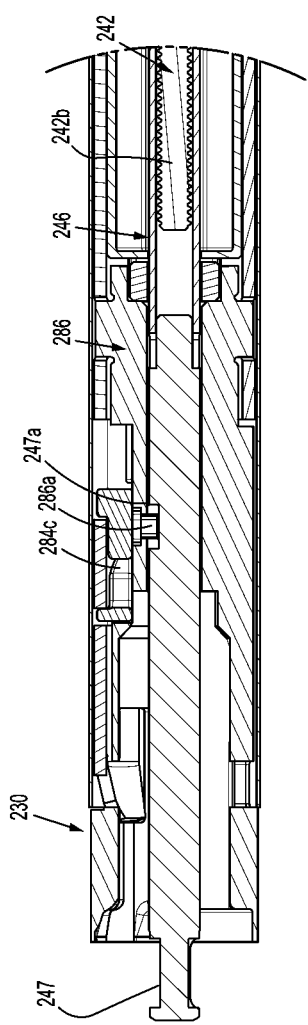
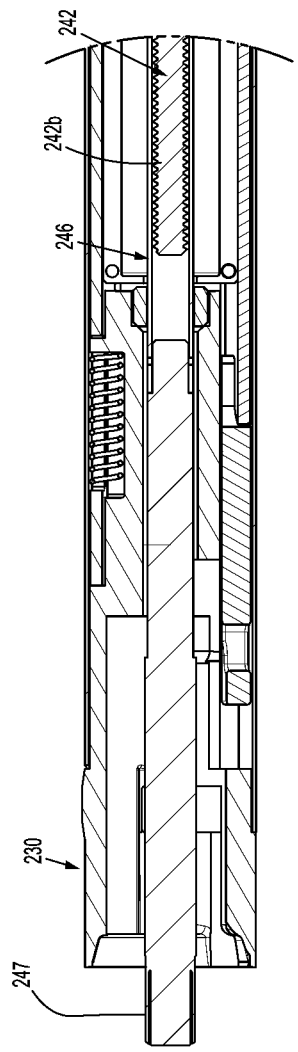
FIG. 18
FIG. 19

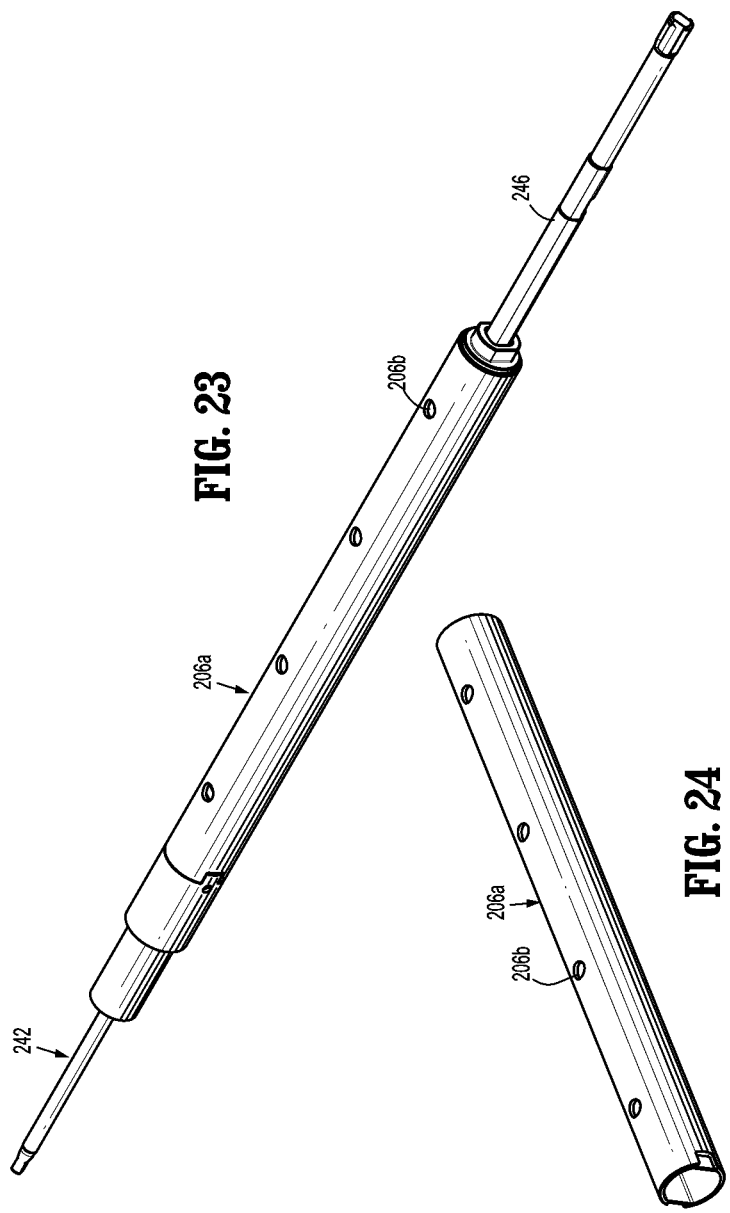

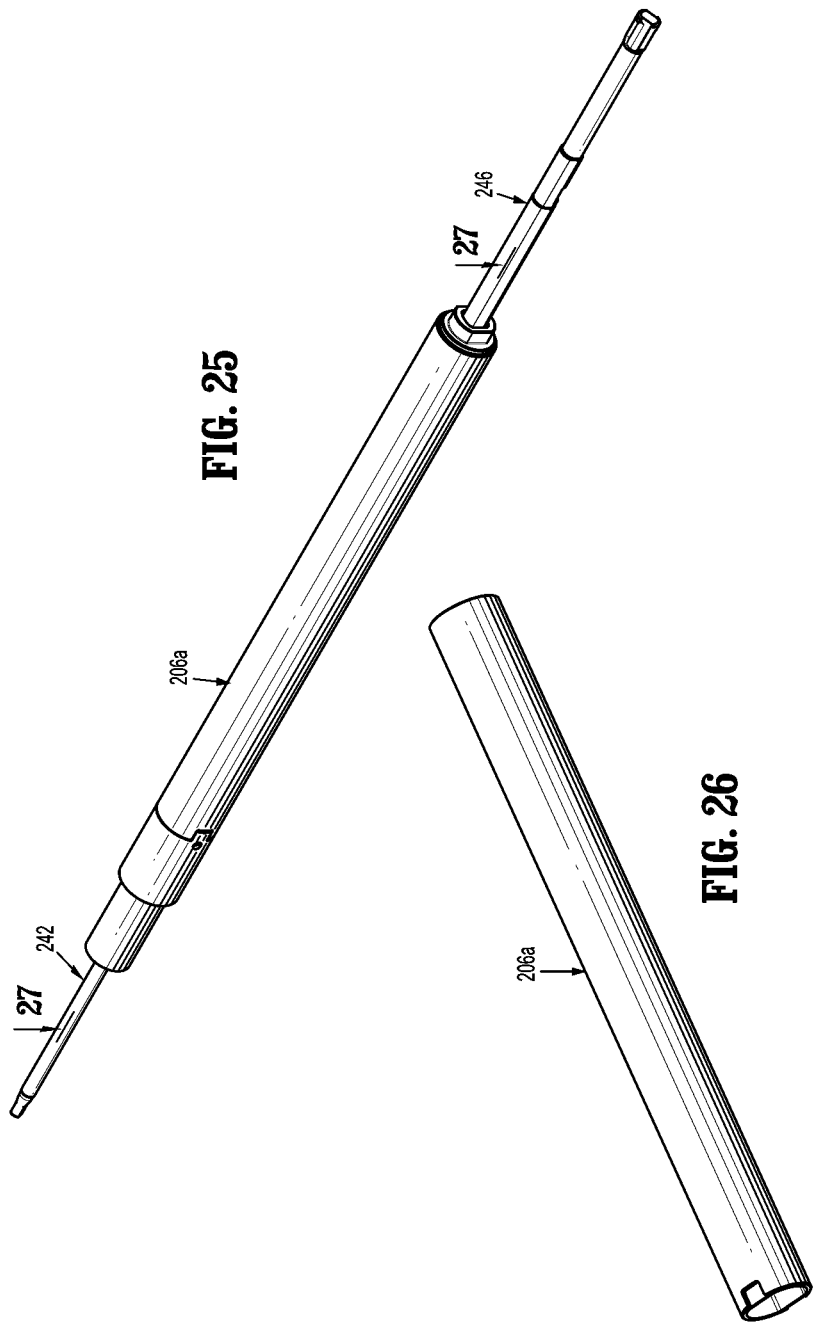

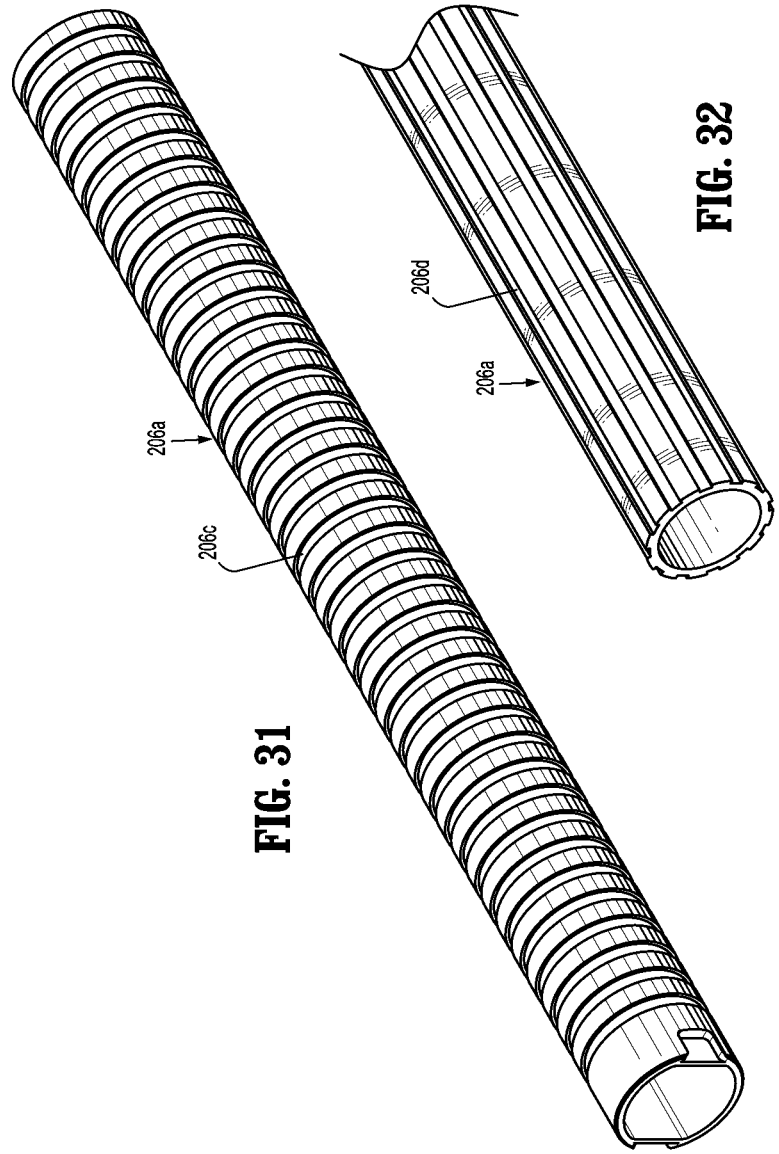

HAND HELD SURGICAL HANDLE ASSEMBLY, SURGICAL ADAPTERS FOR USE BETWEEN SURGICAL HANDLE ASSEMBLY AND SURGICAL END EFFECTORS, AND METHODS OF USE

CROSS REFERENCE TO RELATED APPLICATION

The present application is a Continuation-in-Part Application claiming the benefit of and priority to U.S. patent application Ser. No. 13/331,047, filed on Dec. 20, 2011 now U.S. Pat. No. 8,968,276, which is a Continuation-in-Part Application claiming the benefit of and priority to U.S. patent application Ser. No. 12/946,082, filed on Nov. 15, 2010 now U.S. Pat. No. 8,806,973, which claims the benefit of and priority to each of U.S. Provisional Application Ser. No. 61/308,045, filed on Feb. 25, 2010, and U.S. Provisional Application Ser. No. 61/265,942, filed on Dec. 2, 2009, the entire content of each of which being incorporate herein by reference.

U.S. patent application Ser. No. 13/331,047, filed on Dec. 20, 2011, is a Continuation-in-Part Application claiming the benefit of and priority to U.S. patent application Ser. No. 12/758,900, filed on Apr. 13, 2010, which is a Continuation-in-Part Application claiming the benefit of and priority to U.S. patent application Ser. No. 12/622,827, filed on Nov. 20, 2009, the entire content of each of which being incorporated herein by reference.

U.S. patent application Ser. No. 13/331,047, filed on Dec. 20, 2011, is a Continuation-in-Part Application claiming the benefit of and priority to U.S. patent application Ser. No. 13/089,672, filed on Apr. 19, 2011 now U.S. Pat. No. 9,342,379, which is a Divisional Application claiming the benefit of and priority to U.S. patent application Ser. No. 12/235,362, filed on Sep. 22, 2008 (now U.S. Pat. No. 7,963,433), which claims the benefit of and priority to U.S. Provisional Patent Application Ser. No. 60/974,267, filed on Sep. 21, 2007, the entire content of each of which being incorporated herein by reference.

U.S. patent application Ser. No. 13/331,047, filed on Dec. 20, 2011, is a Continuation-in-Part Application claiming the benefit of and priority to U.S. patent application Ser. No. 13/089,473, filed on Apr. 19, 2011, which is a Divisional Application claiming the benefit of and priority to U.S. patent application Ser. No. 12/235,362, filed on Sep. 22, 2008 (now U.S. Pat. No. 7,963,433), which claims the benefit of and priority to U.S. Provisional Patent Application Ser. No. 60/974,267, filed on Sep. 21, 2007, the entire content of each of which being incorporated herein by reference.

U.S. patent application Ser. No. 13/331,047, filed on Dec. 20, 2011, is a Continuation-in-Part Application claiming the benefit of and priority to U.S. patent application Ser. No. 13/090,286, filed on Apr. 20, 2011 now U.S. Pat. No. 8,272,554, which is a Divisional Application claiming the benefit of and priority to U.S. patent application Ser. No. 12/235,362, filed on Sep. 22, 2008 (now U.S. Pat. No. 7,963,433), which claims the benefit of and priority to U.S. Provisional Patent Application Ser. No. 60/974,267, filed on Sep. 21, 2007, the entire content of each of which being incorporated herein by reference.

BACKGROUND

1. Technical Field

The present disclosure relates to surgical devices and/or systems, surgical adapters and their methods of use. More specifically, the present disclosure relates to hand held powered surgical devices, surgical adapters and/or adapter assemblies for use between and for interconnecting the powered, rotating and/or articulating surgical device or handle assembly and an end effector for clamping, cutting and/or stapling tissue.

2. Background of Related Art

One type of surgical device is a linear clamping, cutting and stapling device. Such a device may be employed in a surgical procedure to resect a cancerous or anomalous tissue from a gastro-intestinal tract. Conventional linear clamping, cutting and stapling instruments include a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A number of surgical device manufacturers have developed product lines with proprietary drive systems for operating and/or manipulating the surgical device. In many instances the surgical devices include a handle assembly, which is reusable, and a disposable end effector or the like that is selectively connected to the handle assembly prior to use and then disconnected from the end effector following use in order to be disposed of or in some instances sterilized for re-use.

Many of the existing end effectors for use with many of the existing surgical devices and/or handle assemblies are driven by a linear force. For examples, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use a rotary motion to deliver power or the like.

In order to make the linear driven end effectors compatible with surgical devices and/or handle assemblies that use a rotary motion to deliver power, a need exists for adapters and/or adapter assemblies to interface between and interconnect the linear driven end effectors with the rotary driven surgical devices and/or handle assemblies.

SUMMARY

The present disclosure relates to hand held powered surgical devices, surgical adapters and/or adapter assemblies for use between and for interconnecting the powered, rotating and/or articulating surgical device or handle assembly and an end effector for clamping, cutting and/or stapling tissue.

According to an aspect of the present disclosure, an electromechanical surgical system is provided, comprising a hand-held surgical device, including a device housing defining a connecting portion for selectively connecting with an adapter assembly; at least one drive motor supported in the device housing and being configured to rotate a drive shaft; a power source (e.g., a battery, a fuel cell, a power cord connected to an external power source, etc.) disposed within the device housing for powering the at least one drive motor; and a circuit board disposed within the housing for controlling power delivered from the battery to the motor. The electromechanical surgical system further comprises an end effector configured to perform at least one function, the end effector including at least one axially translatable drive member; and an adapter assembly for selectively interconnecting the end effector and the surgical device. The adapter assembly includes an adapter housing configured and adapted for selective connection to the connecting portion of the surgical device and to be in operative communication with each of the at least one rotatable drive shaft of the surgical device; an outer tube having a proximal end supported by the adapter housing and a distal end configured and adapted for connection with the end effector, wherein the distal end of the outer tube is in operative communication with each of the at least one axially translatable drive member of the end effector; at least one drive converter assembly for interconnecting a respective one of the at least one rotatable drive shaft of the surgical device and one of the at least one axially translatable drive member of the end effector, wherein the at least one drive converter assembly includes a first end that is connectable to a drive shaft of the surgical device and a second end that is connectable to the at least one axially translatable drive member of the end effector, wherein the at least one drive converter assembly converts and transmits a rotation of the rotatable drive shaft of the surgical device to an axial translation of the at least one axially translatable drive member of the end effector.

The at least one drive converter assembly of the adapter assembly may include a first drive converter assembly including a first distal drive shaft rotatably supported in the adapter housing, wherein a proximal end of the first distal drive shaft is connectable to the rotatable drive shaft of the surgical device; a drive coupling nut threadably connected to a threaded distal portion of the first distal drive shaft, wherein the drive coupling nut is keyed against rotation within the adapter housing; and a drive tube having a proximal end connected to the drive coupling nut and a distal end configured for selective engagement with the at least one axially translatable drive member of the end effector. Wherein rotation of the rotatable drive shaft of the surgical device results in rotation of the distal drive shaft. Wherein rotation of the distal drive shaft results in axial translation of the drive coupling nut, the drive tube and the at least one axially translatable drive member of the end effector.

The first drive converter assembly may include a spur gear keyed to the proximal end of the distal drive shaft; a proximal rotatable drive shaft having a spur gear supported on a distal end thereof and a proximal end connectable to the rotatable drive shaft of the surgical device; and a compound gear interengaging the spur gear keyed to the proximal end of the distal drive shaft and the spur gear supported on the distal end of the proximal rotatable drive shaft.

The electromechanical surgical system may further comprise a connector sleeve interconnecting the rotatable drive shaft of the surgical device with the proximal rotatable drive shaft of the adapter assembly.

In use, translation of the at least one axially translatable drive member of the end effector results in a closing of the end effector and a firing of the end effector.

The at least one drive converter assembly of the adapter assembly may include a second drive converter assembly including a second proximal drive shaft rotatably supported in the adapter housing, wherein a proximal end of the second proximal drive shaft is connectable to a second rotatable drive shaft of the surgical device; a coupling cuff rotatably and translatably supported in the adapter housing, the coupling cuff defining an inner annular race; a coupling slider rotatably disposed within the annular race of the coupling cuff, the coupling slider being threadably connected to a threaded distal portion of the second proximal drive shaft; and a drive bar having a proximal end connected to the coupling cuff and a distal end configured for selective engagement with another axially translatable drive member of the end effector. Wherein rotation of the second rotatable drive shaft of the surgical device results in rotation of the second proximal drive shaft. Wherein rotation of the second proximal drive shaft results in axial translation of the coupling slider, the coupling cuff, the drive bar and the another axially translatable drive member of the end effector.

The first distal drive shaft may extend through the coupling cuff such that the coupling cuff is rotatable about the first distal drive shaft.

The electromechanical surgical system may further comprise a connector sleeve interconnecting the second rotatable drive shaft of the device with the second proximal drive shaft of the adapter assembly.

In use, translation of the another axially translatable drive member of the end effector results in an articulation of the end effector relative to the adapter.

The adapter may further comprise a drive transmitting assembly including a third proximal rotatable drive shaft rotatably supported in the adapter housing and having a spur gear supported on a distal end thereof and a proximal end connectable to a third rotatable drive shaft of the surgical device; a ring gear rotatably supported in the adapter housing, the ring gear defining an internal array of gear teeth which are engaged with the spur gear of the third proximal rotatable drive shaft; a rotation housing rotatably supported in the adapter housing and being keyed to the ring gear; and at least one rotation transmitting bar having a proximal end connected to the rotation housing and a distal end connected to a distal coupling assembly, wherein the distal coupling assembly is configured to selective connect with the end effector. Wherein rotation of the third rotatable drive shaft of the surgical device results in rotation of the third proximal drive shaft, and wherein rotation of the third proximal drive shaft results in rotation of the ring gear, the rotation housing, the at least one rotation transmitting bar and the distal coupling assembly to rotate the end effector relative to the adapter and about a longitudinal axis defined by the adapter.

The electromechanical surgical system may thither comprise a connector sleeve interconnecting the third rotatable drive shaft of the device with the third proximal drive shaft of the adapter assembly.

The end effector may be configured for endoscopic insertion into a target surgical site. The outer tube of the adapter may be configured for endoscopic insertion into a target surgical site. The outer tube of the adapter may have an outer dimension of approximately 12 mm. The adapter housing may be inhibited from insertion into the target surgical site.

At least one of the first drive converter assembly, the second drive converter assembly and the drive transmitting assembly may be disposed in the adapter housing.

In an embodiment, the end effector and the outer tube of the adapter define an endoscopic portion that is configured for endoscopic insertion into a target surgical site. Each of the first drive converter assembly, the second drive converter assembly and the drive transmitting assembly may be disposed outside of the endoscopic portion.

According to a further aspect of the present disclosure, an adapter assembly is provided for selectively interconnecting a surgical end effector that is configured to perform a function and a surgical device that is configured to actuate the end effector, the end effector including at least one axially translatable drive member, and the surgical device including at least one rotatable drive shaft. The adapter assembly includes a housing configured and adapted for connection with the surgical device and to be in operative communication with each of the at least one rotatable drive shaft of the surgical device; an inner housing tube having a proximal end supported by the housing, the inner housing tube defining an internal cavity and at least one aperture opening into the cavity, wherein the at least one aperture provides an egress for fluid entering the cavity during at least one of a use and a cleaning of the adapter assembly; and at least one drive converter assembly for interconnecting a respective one of the at least one rotatable drive shaft of the surgical device and one of the at least one axially translatable drive member of the end effector, wherein the at least one drive converter assembly is at least partially disposed within the cavity of the inner housing tube.

The at least one drive converter assembly includes a first end that is connectable to a first rotatable drive shaft of the surgical device; and a second end that is connectable to a first axially translatable drive member of the end effector, wherein the at least one drive converter assembly converts and transmits a rotation of the first rotatable drive shaft of the surgical device to an axial translation of the first axially translatable drive member of the end effector.

The at least one aperture formed in the inner housing tube may include a plurality of apertures disposed along one side of the inner housing tube and extending along a length thereof. The plurality of apertures formed in the inner housing tube may extend substantially in a longitudinal direction. The plurality of apertures formed in the inner housing tube may include apertures disposed on opposed sides of the inner housing tube.

According to yet another aspect of the present disclosure, an adapter assembly is provided for selectively interconnecting a surgical end effector that is configured to perform a function and a surgical device that is configured to actuate the end effector, the end effector including at least one axially translatable drive member, and the surgical device including at least one rotatable drive shaft. The adapter assembly includes a housing configured and adapted for connection with the surgical device and to be in operative communication with each of the at least one rotatable drive shaft of the surgical device; an inner housing tube having a proximal end supported by the housing, the inner housing tube defining an internal cavity and at least one aperture opening into the cavity; a distal coupling assembly disposed at a distal end of the inner housing tube, wherein the distal coupling assembly is configured to selectively connect with the end effector; at least one drive converter assembly for interconnecting a respective one of the at least one rotatable drive shaft of the surgical device and one of the at least one axially translatable drive member of the end effector, wherein the at least one drive converter assembly is at least partially disposed within the cavity of the inner housing tube; and a plurality of seals disposed between the inner housing tube and the at least one drive converter assembly so as to prevent ingress of fluid into the cavity of the inner housing tube.

The at least one drive converter assembly includes a first end that is connectable to a first rotatable drive shaft of the surgical device; and a second end that is connectable to a first axially translatable drive member of the end effector, wherein the at least one drive converter assembly converts and transmits a rotation of the first rotatable drive shaft of the surgical device to an axial translation of the first axially translatable drive member of the end effector.

The plurality of seals may include a first seal interposed between the distal coupling assembly and a drive tube of the at least one drive converter assembly. The first seal may be a bi-directional seal. The bi-direction seal may be an X-ring gasket.

The plurality of seals may include a second seal interposed between the distal coupling assembly and the inner housing tube. The second seal may be a compression sleeve.

The plurality of seals may include a third seal recessed within a proximal bushing of the adapter assembly. The third seal may be one of an 0-ring gasket and an X-ring gasket.

The plurality of seals may include a fourth seal recessed within an inner diameter of the proximal bushing of adapter assembly to ride on an outer diameter of a first distal drive shaft of the at least one drive converter assembly. The fourth seal may be one of an O-ring gasket and an X-ring gasket.

According to still another aspect of the present disclosure, an adapter assembly is provided for selectively interconnecting a surgical end effector that is configured to perform a function and a surgical device that is configured to actuate the end effector, the end effector including at least one axially translatable drive member, and the surgical device including at least one rotatable drive shaft. The adapter assembly includes a housing configured and adapted for connection with the surgical device and to be in operative communication with each of the at least one rotatable drive shaft of the surgical device; an inner housing tube having a proximal end supported by the housing, the inner housing tube defining an internal cavity and at least one heat dissipation feature provided on an exterior surface of inner housing tube; and at least one drive converter assembly for interconnecting a respective one of the at least one rotatable drive shaft of the surgical device and one of the at least one axially translatable drive member of the end effector, wherein the at least one drive converter assembly is at least partially disposed within the cavity of the inner housing tube. The at least one drive converter assembly includes a first end that is connectable to a first rotatable drive shaft of the surgical device; and a second end that is connectable to a first axially translatable drive member of the end effector, wherein the at least one drive converter assembly converts and transmits a rotation of the first rotatable drive shaft of the surgical device to an axial translation of the first axially translatable drive member of the end effector.

The at least one heat dissipation feature may include at least one groove formed in the outer surface of the inner tube. The at least one groove may include a plurality of grooves defining a plurality of ridges on the outer surface of the inner tube.

The plurality of grooves may extend annularly about the outer surface of the inner tube.

The plurality of grooves may extend longitudinally along the outer surface of the inner tube.

BRIEF DESCRIPTION OF THE DRAWINGS

Embodiments of the present disclosure are described herein with reference to the accompanying drawings, wherein:

FIG. 4 is a perspective view of a battery for use in the surgical device of FIGS. 1-3;

FIG. 5 is a perspective view of the surgical device of FIGS. 1-3, with a housing thereof removed;

FIG. 18 is an enlarged view of the indicated area of detail of 14;

FIG. 19 is an enlarged view of the indicated area of detail of 15;

FIG. 23 is a first perspective view of an inner housing tube of an adapter according to another embodiment of the present disclosure;

FIG. 24 is a second perspective view of the inner housing tube of FIG. 23;

FIG. 25 is a first perspective view of an inner housing tube according to a further embodiment of the present disclosure;

FIG. 26 is a second perspective view of the inner housing tube of FIG. 25;

FIG. 31 is a perspective view of an inner housing tube of an adapter according to yet another embodiment of the present disclosure; and FIG. 32 is a perspective view of an inner housing tube of an adapter according to another embodiment of the present disclosure.

DETAILED DESCRIPTION OF EMBODIMENTS

Figure 1:
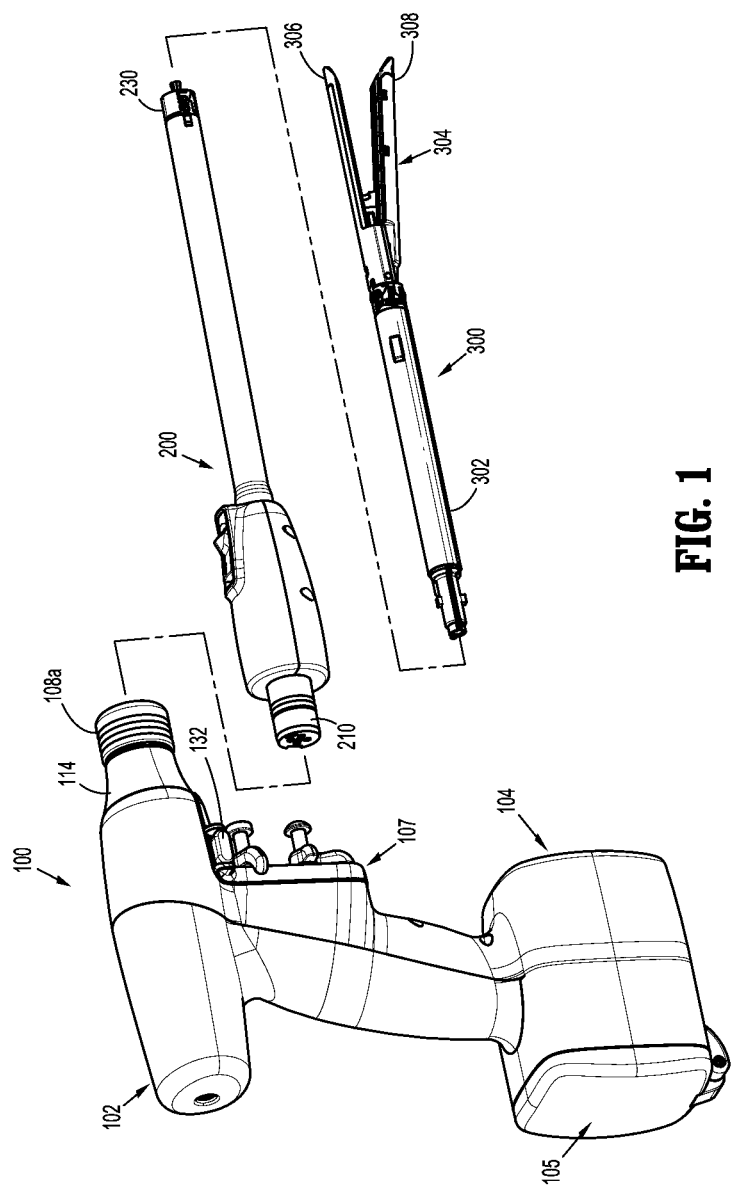
FIG. 1 is a perspective view, with parts separated, of a surgical device and adapter, in accordance with an embodiment of the present disclosure, illustrating a connection thereof with an end effector.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered hand held electromechanical instrument configured for selective attachment thereto of a plurality of different end effectors that are each configured for actuation and manipulation by the powered hand held electromechanical surgical instrument.

As illustrated in FIG. 1, surgical device 100 is configured for selective connection with an adapter 200, and, in turn, adapter 200 is configured for selective connection with an end effector or single use loading unit 300.

Figure 2:
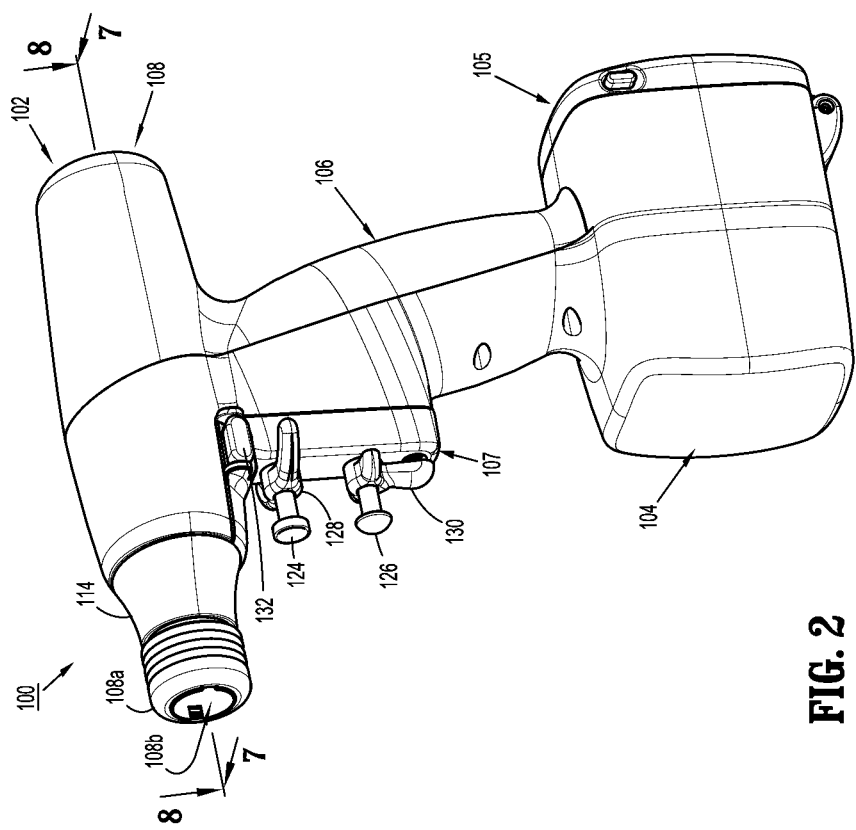
FIG. 2 is a perspective view of the surgical device of FIG. 1.
Figure 3:
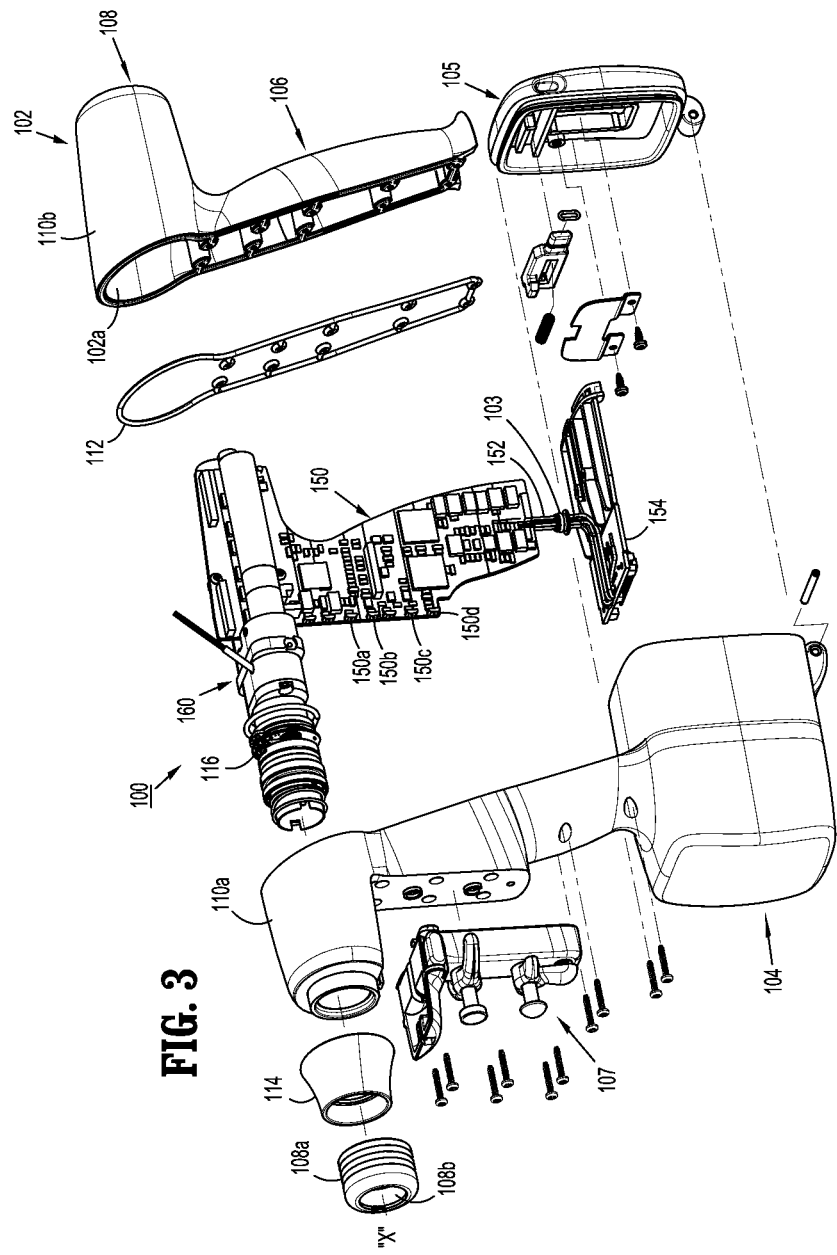
FIG. 3 is a perspective view, with parts separated, of the surgical device of FIGS. 1 and 2.

As illustrated in FIGS. 1-3, surgical device 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 is situated.

Distal and proximal half-sections 110a, 110b are divided along a plane that traverses a longitudinal axis "X" of upper housing portion 108, as seen in FIG. 1.

Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical device 100, as will be set forth in additional detail below.

Lower housing portion 104 of surgical device 100 defines an aperture (not shown) formed in an upper surface thereof and which is located beneath or within intermediate housing portion 106. The aperture of lower housing portion 104 provides a passage through which wires 152 pass to electrically interconnect electrical components (a battery 156, as illustrated in FIG. 4, a circuit board 154, as illustrated in FIG. 3, etc.) situated in lower housing portion 104 with electrical components (circuit board 150, drive mechanism 160, etc.) situated in intermediate housing portion 106 and/or upper housing portion 108.

Handle housing 102 includes a gasket 103 disposed within the aperture of lower housing portion 104 (not shown) thereby plugging or sealing the aperture of lower housing portion 104 while allowing wires 152 to pass therethrough. Gasket 103 functions to establish an airtight seal between lower housing portion 106 and intermediate housing portion 108 such that circuit board 150 and drive mechanism 160 are protected from sterilization and/or cleaning procedures.

As shown, lower housing portion 104 of handle housing 102 provides a housing in which a rechargeable battery 156, is removably situated. Battery 156 is configured to supply power to any of the electrical components of surgical device 100. Lower housing portion 104 defines a cavity (not shown) into which battery 156 is inserted. Lower housing portion 104 includes a door 105 pivotally connected thereto for closing cavity of lower housing portion 104 and retaining battery 156 therein. While a battery 156 is shown, it is contemplated that the surgical device may be powered by any number of power sources, such as, for example, a fuel cell, a power cord connected to an external power source, etc.

With reference to FIGS. 3 and 5, distal half-section 110a of upper housing portion 108 defines a nose or connecting portion 108a. A nose cone 114 is supported on nose portion 108a of upper housing portion 108. Nose cone 114 is fabricated from a transparent material. An illumination member 116 is disposed within nose cone 114 such that illumination member 116 is visible therethrough. Illumination member 116 is in the form of a light emitting diode printed circuit board (LED PCB). Illumination member 116 is configured to illuminate multiple colors with a specific color pattern being associated with a unique discrete event.

Upper housing portion 108 of handle housing 102 provides a housing in which drive mechanism 160 is situated. As illustrated in FIG. 5, drive mechanism 160 is configured to drive shafts and/or gear components in order to perform the various operations of surgical device 100. In particular, drive mechanism 160 is configured to drive shafts and/or gear components in order to selectively move tool assembly 304 of end effector 300 (see FIGS. 1 and 20) relative to proximal body portion 302 of end effector 300, to rotate end effector 300 about a longitudinal axis "X" (see FIG. 3) relative to handle housing 102, to move anvil assembly 306 relative to cartridge assembly 308 of end effector 300, and/or to fire a stapling and cutting cartridge within cartridge assembly 308 of end effector 300.

The drive mechanism 160 includes a selector gearbox assembly 162 that is located immediately proximal relative to adapter 200. Proximal to the selector gearbox assembly 162 is a function selection module 163 having a first motor 164 that functions to selectively move gear elements within the selector gearbox assembly 162 into engagement with an input drive component 165 having a second motor 166.

As illustrated in FIGS. 1-4, and as mentioned above, distal half-section 110a of upper housing portion 108 defines a connecting portion 108a configured to accept a corresponding drive coupling assembly 210 of adapter 200.

Figure 6:
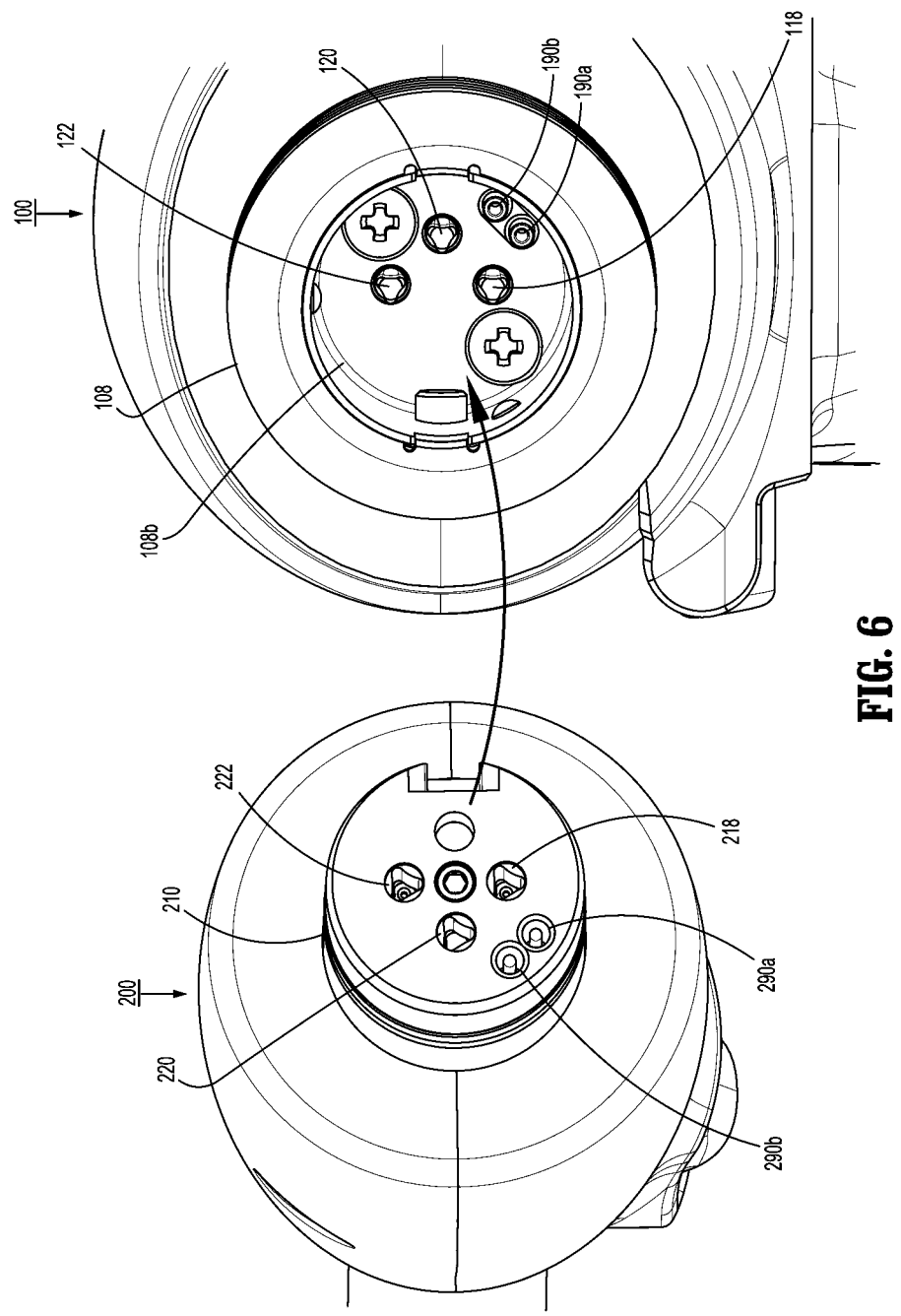
FIG. 6 is a perspective view of the connecting ends of each of the surgical device and the adapter, illustrating a connection therebetween.
Figure 7:
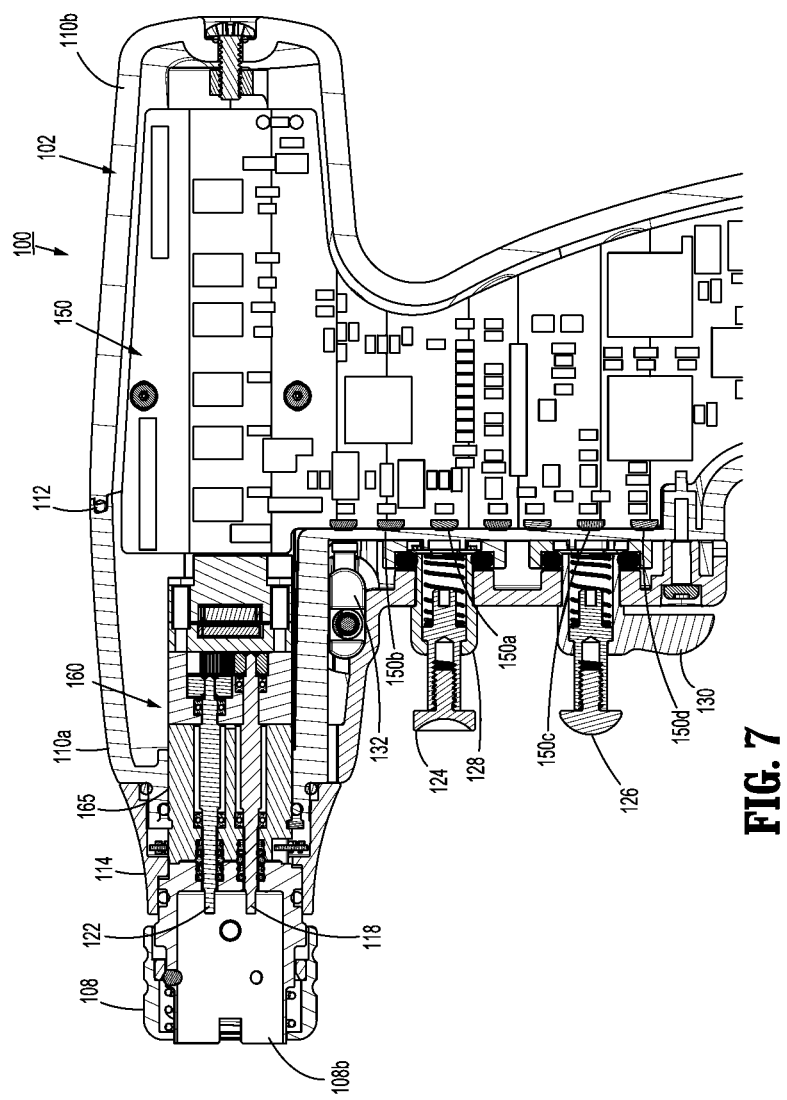
FIG. 7 is a cross-sectional view of the surgical device of FIGS. 1-3, as taken through 7-7 of FIG. 2.
Figure 8:
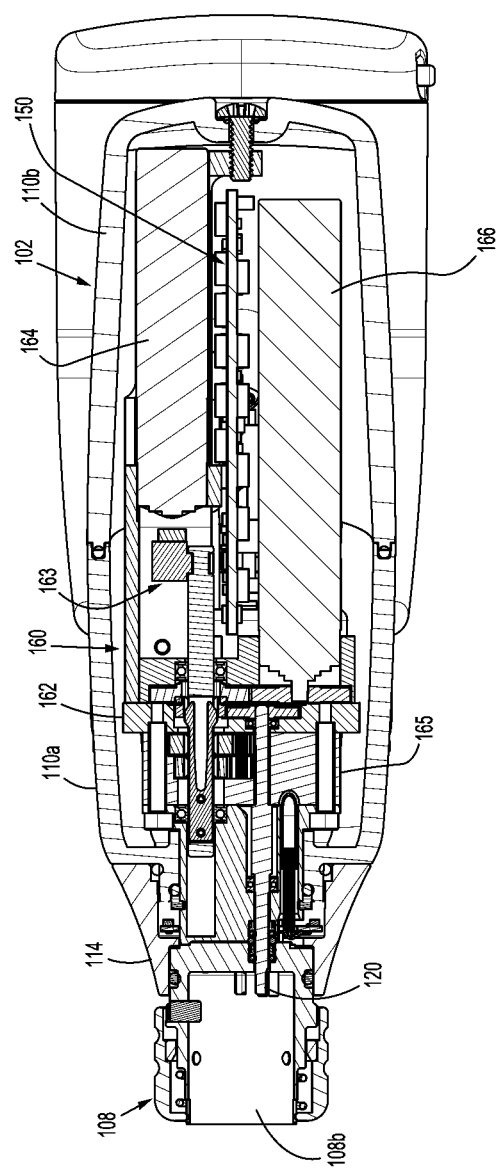
FIG. 8 is a cross-sectional view of the surgical device of FIGS. 1-3, as taken through 8-8 of FIG. 2.
Figure 9:
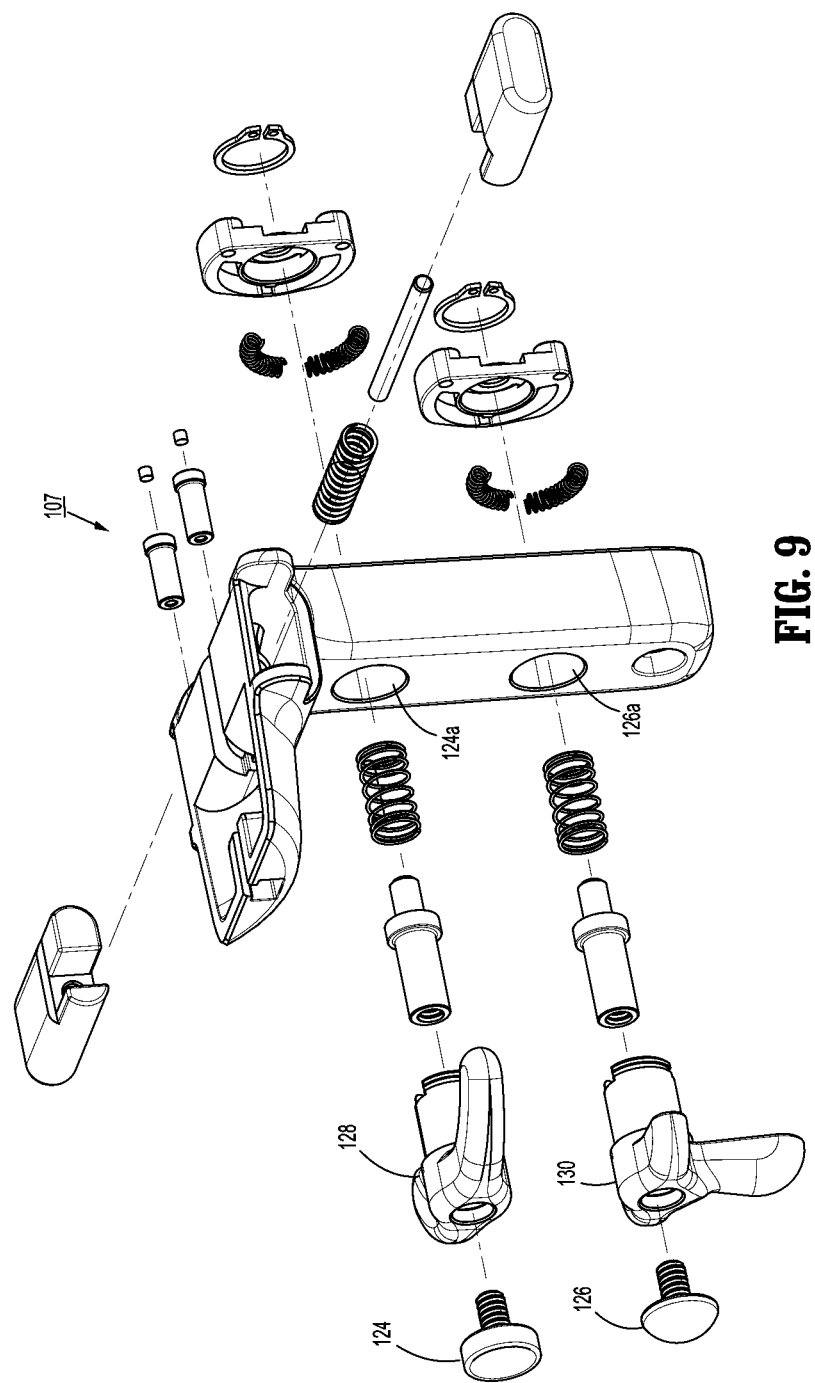
FIG. 9 is a perspective view, with parts separated, of a trigger housing of the surgical device of FIGS. 1-3.

As illustrated in FIGS. 6-8, connecting portion 108a of surgical device 100 has a cylindrical recess 108b that receives a drive coupling assembly 210 of adapter 200 when adapter 200 is mated to surgical device 100. Connecting portion 108a houses three rotatable drive connectors 118, 120, 122.

When adapter 200 is mated to surgical device 100, each of rotatable drive connectors 118, 120, 122 of surgical device 100 couples with a corresponding rotatable connector sleeve 218, 220, 222 of adapter 200. (see FIG. 6). In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical device 100 causes a corresponding rotation of the corresponding connector sleeve 218, 220, 222 of adapter 200.

The mating of drive connectors 118, 120, 122 of surgical device 100 with connector sleeves 218, 220, 222 of adapter 200 allows rotational forces to be independently transmitted via each of the three respective connector interfaces. The drive connectors 118, 120, 122 of surgical device 100 are configured to be independently rotated by drive mechanism 160. In this regard, the function selection module 163 of drive mechanism 160 selects which drive connector or connectors 118, 120, 122 of surgical device 100 is to be driven by the input drive component 165 of drive mechanism 160.

Since each of drive connectors 118, 120, 122 of surgical device 100 has a keyed and/or substantially non-rotatable interface with respective connector sleeves 218, 220, 222 of adapter 200, when adapter 200 is coupled to surgical device 100, rotational force(s) are selectively transferred from drive mechanism 160 of surgical device 100 to adapter 200.

The selective rotation of drive connector(s) 118, 120 and/or 122 of surgical device 100 allows surgical device 100 to selectively actuate different functions of end effector 300. As will be discussed in greater detail below, selective and independent rotation of first drive connector 118 of surgical device 100 corresponds to the selective and independent opening and closing of tool assembly 304 of end effector 300, and driving of a stapling/cutting component of tool assembly 304 of end effector 300. Also, the selective and independent rotation of second drive connector 120 of surgical device 100 corresponds to the selective and independent articulation of tool assembly 304 of end effector 300 transverse to longitudinal axis "X" (see FIG. 3). Additionally, the selective and independent rotation of third drive connector 122 of surgical device 100 corresponds to the selective and independent rotation of end effector 300 about longitudinal axis "X" (see FIG. 3) relative to handle housing 102 of surgical device 100.

As mentioned above and as illustrated in FIGS. 5 and 8, drive mechanism 160 includes a selector gearbox assembly 162; a function selection module 163, located proximal to the selector gearbox assembly 162, that functions to selectively move gear elements within the selector gearbox assembly 162 into engagement with second motor 166. Thus, drive mechanism 160 selectively drives one of drive connectors 118, 120, 122 of surgical device 100 at a given time.

As illustrated in FIGS. 1-3 and FIG. 9, handle housing 102 supports a trigger housing 107 on a distal surface or side of intermediate housing portion 108. Trigger housing 107, in cooperation with intermediate housing portion 108, supports a pair of finger-actuated control buttons 124, 126 and rocker devices 128, 130. In particular, trigger housing 107 defines an upper aperture 124a for slidably receiving a first control button 124, and a lower aperture 126b for slidably receiving a second control button 126.

Each one of the control buttons 124, 126 and rocker devices 128, 130 includes a respective magnet (not shown) that is moved by the actuation of an operator. In addition, circuit board 150 includes, for each one of the control buttons 124, 126 and rocker devices 128, 130, respective Hall-effect switches 150a-150d that are actuated by the movement of the magnets in the control buttons 124, 126 and rocker devices 128, 130. In particular, located immediately proximal to the control button 124 is a first Hall-effect switch 150a (see FIGS. 3 and 7) that is actuated upon the movement of a magnet within the control button 124 upon the operator actuating control button 124. The actuation of first Hall-effect switch 150a, corresponding to control button 124, causes circuit board 150 to provide appropriate signals to function selection module 163 and input drive component 165 of the drive mechanism 160 to close a tool assembly 304 of end effector 300 and/or to fire a stapling/cutting cartridge within tool assembly 304 of end effector 300.

Also, located immediately proximal to rocker device 128 is a second Hall-effect switch 150b (see FIGS. 3 and 7) that is actuated upon the movement of a magnet (not shown) within rocker device 128 upon the operator actuating rocker device 128. The actuation of second Hall-effect switch 150b, corresponding to rocker device 128, causes circuit board 150 to provide appropriate signals to function selection module 163 and input drive component 165 of drive mechanism 160 to articulate tool assembly 304 relative to body portion 302 of end effector 300. Advantageously, movement of rocker device 128 in a first direction causes tool assembly 304 to articulate relative to body portion 302 in a first direction, while movement of rocker device 128 in an opposite, e.g., second, direction causes tool assembly 304 to articulate relative to body portion 302 in an opposite, e.g., second, direction.

Furthermore, located immediately proximal to control button 126 is a third Hall-effect switch 150c (see FIGS. 3 and 7) that is actuated upon the movement of a magnet (not shown) within control button 126 upon the operator actuating control button 126. The actuation of third Hall-effect switch 150c, corresponding to control button 126, causes circuit board 150 to provide appropriate signals to function selection module 163 and input drive component 165 of drive mechanism 160 to open tool assembly 304 of end effector 300.

In addition, located immediately proximal to rocker device 130 is a fourth Hall-effect switch 150d (see FIGS. 3 and 7) that is actuated upon the movement of a magnet (not shown) within rocker device 130 upon the operator actuating rocker device 130. The actuation of fourth Hall-effect switch 150d, corresponding to rocker device 130, causes circuit board 150 to provide appropriate signals to function selection module 163 and input drive component 165 of drive mechanism 160 to rotate end effector 300 relative to handle housing 102 surgical device 100. Specifically, movement of rocker device 130 in a first direction causes end effector 300 to rotate relative to handle housing 102 in a first direction, while movement of rocker device 130 in an opposite, e.g., second, direction causes end effector 300 to rotate relative to handle housing 102 in an opposite, e.g., second, direction.

As seen in FIGS. 1-3, surgical device 100 includes a fire button or safety switch 132 supported between intermediate housing portion 108 and upper housing portion, and situated above trigger housing 107. In use, tool assembly 304 of end effector 300 is actuated between opened and closed conditions as needed and/or desired. In order to fire end effector 300, to expel fasteners therefrom when tool assembly 304 of end effector 300 is in a closed condition, safety switch 132 is depressed thereby instructing surgical device 100 that end effector 300 is ready to expel fasteners therefrom.

As illustrated in FIGS. 1 and 10-20, surgical device 100 is configured for selective connection with adapter 200, and, in turn, adapter 200 is configured for selective connection with end effector 300.

Figure 21:
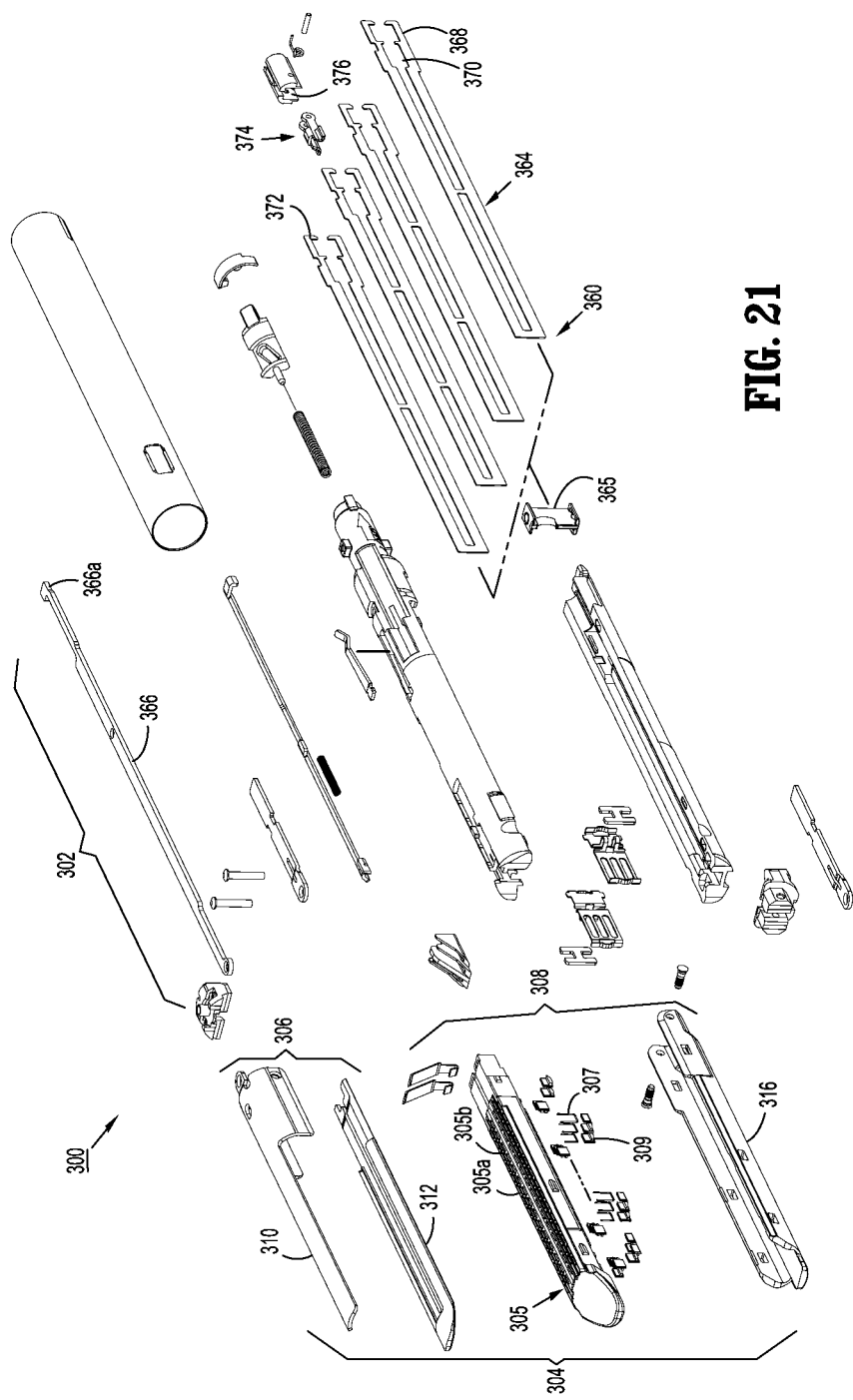
FIG. 21 is a perspective view, with parts separated, of an exemplary end effector for use with the surgical device and the adapter of the present disclosure.

Adapter 200 is configured to convert a rotation of either of drive connectors 120 and 122 of surgical device 100 into axial translation useful for operating a drive assembly 360 and an articulation link 366 of end effector 300, as illustrated in FIG. 21 and as will be discussed in greater detail below.

Adapter 200 includes a first drive transmitting/converting assembly for interconnecting third rotatable drive connector 122 of surgical device 100 and a first axially translatable drive member of end effector 300, wherein the first drive transmitting/converting assembly converts and transmits a rotation of third rotatable drive connector 122 of surgical device 100 to an axial translation of the first axially translatable drive assembly 360 of end effector 300 for firing.

Adapter 200 includes a second drive transmitting/converting assembly for interconnecting second rotatable drive connector 120 of surgical device 100 and a second axially translatable drive member of end effector 300, wherein the second drive transmitting/converting assembly converts and transmits a rotation of second rotatable drive connector 120 of surgical device 100 to an axial translation of articulation link 366 of end effector 300 for articulation.

Figure 10:
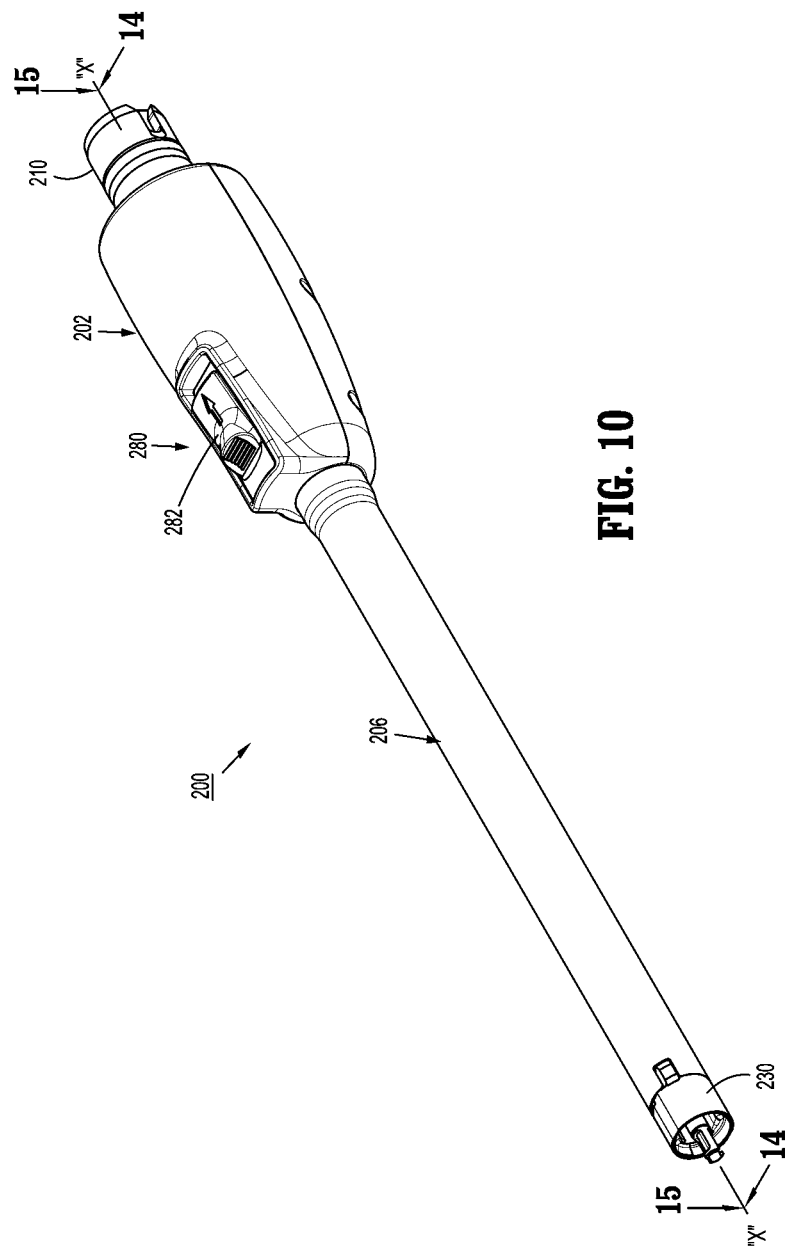
FIG. 10 is a perspective view of the adapter of FIG. 1.
Figure 11:
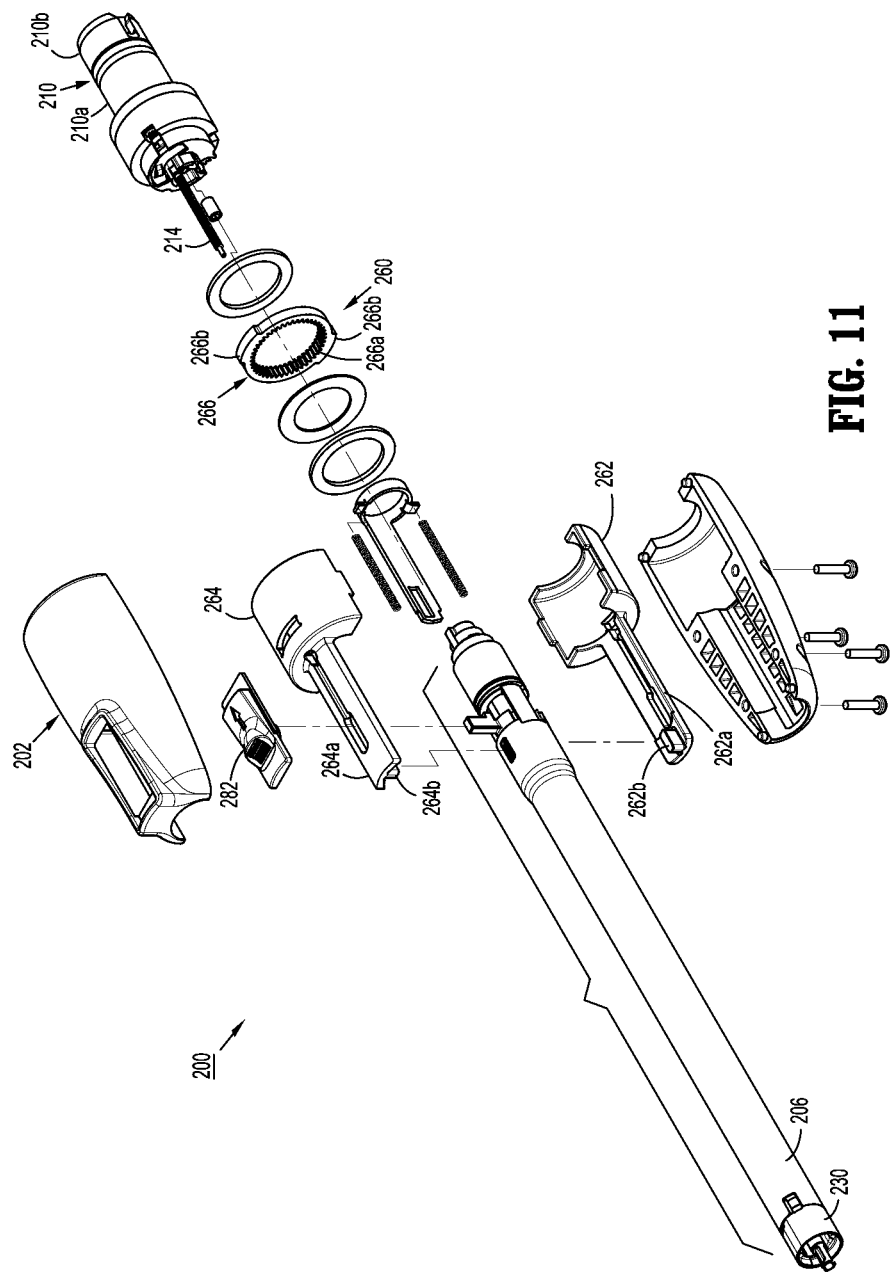
FIG. 11 is a perspective view, with parts separated, of the adapter of FIGS. 1 and 10.

Turning now to FIGS. 10 and 11, adapter 200 includes a knob housing 202 and an outer tube 206 extending from a distal end of knob housing 202. Knob housing 202 and outer tube 206 are configured and dimensioned to house the components of adapter 200. Outer tube 206 is dimensioned for endoscopic insertion, in particular, that outer tube is passable through a typical trocar port, cannula or the like. Knob housing 202 is dimensioned to not enter the trocar port, cannula of the like.

Knob housing 202 is configured and adapted to connect to connecting portion 108a of upper housing portion 108 of distal half-section 110a of surgical device 100.

Figure 12:
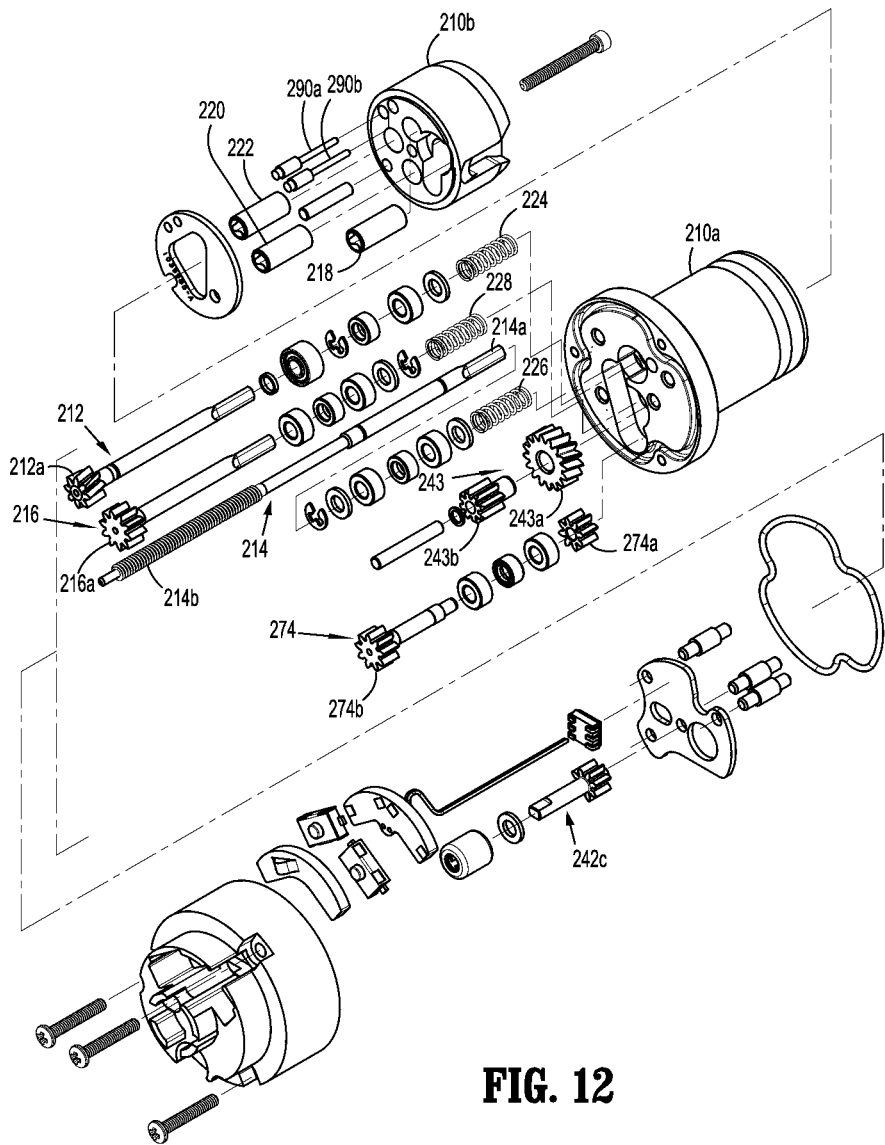
FIG. 12 is a perspective view, with parts separated, of a drive coupling assembly of the adapter of FIGS. 1 and 10.

As seen in FIGS. 10-12, adapter 200 includes a surgical device drive coupling assembly 210 at a proximal end thereof and to an end effector coupling assembly 230 at a distal end thereof. Drive coupling assembly 210 includes a distal drive coupling housing 210a and a proximal drive coupling housing 210b rotatably supported, at least partially, in knob housing 202. Drive coupling assembly 210 rotatably supports a first rotatable proximal drive shaft 212, a second rotatable proximal drive shaft 214, and a third rotatable proximal drive shaft 216 therein.

Proximal drive coupling housing 210b is configured to rotatably support first, second and third connector sleeves 218, 220 and 222, respectively. Each of connector sleeves 218, 220, 222 is configured to mate with respective first, second and third drive connectors 118, 120, 122 of surgical device 100, as described above. Each of connector sleeves 218, 220, 222 is further configured to mate with a proximal end of respective first, second and third proximal drive shafts 212, 214, 216.

Proximal drive coupling assembly 210 includes a first, a second and a third biasing member 224, 226 and 228 disposed distally of respective first, second and third connector sleeves 218, 220, 222. Each of biasing members 224, 226 and 228 is disposed about respective first, second and third rotatable proximal drive shaft 212, 214 and 216. Biasing members 224, 226 and 228 act on respective connector sleeves 218, 220 and 222 to help maintain connector sleeves 218, 220 and 222 engaged with the distal end of respective drive rotatable drive connectors 118, 120, 122 of surgical device 100 when adapter 200 is connected to surgical device 100.

In particular, first, second and third biasing members 224, 226 and 228 function to bias respective connector sleeves 218, 220 and 222 in a proximal direction. In this manner, during assembly of adapter 200 to surgical device 100, if first, second and or third connector sleeves 218, 220 and/or 222 is/are misaligned with the drive connectors 118, 120, 122 of surgical device 100, first, second and/or third biasing member(s) 224, 226 and/or 228 are compressed. Thus, when drive mechanism 160 of surgical device 100 is engaged, drive connectors 118, 120, 122 of surgical device 100 will rotate and first, second and/or third biasing member(s) 224, 226 and/or 228 will cause respective first, second and/or third connector sleeve(s) 218, 220 and/or 222 to slide back proximally, effectively coupling drive connectors 118, 120, 122 of surgical device 100 to first, second and/or third proximal drive shaft(s) 212, 214 and 216 of proximal drive coupling assembly 210.

Upon calibration of surgical device 100, each of drive connectors 118, 120, 122 of surgical device 100 is rotated and the bias on connector sleeve(s) 218, 220 and 222 properly seats connector sleeve(s) 218, 220 and 222 over the respective drive connectors 118, 120, 122 of surgical device 100 when the proper alignment is reached.

Adapter 200 includes a first, a second and a third drive transmitting/converting assembly 240, 250, 260, respectively, disposed within handle housing 202 and outer tube 206. Each drive transmitting/converting assembly 240, 250, 260 is configured and adapted to transmit or convert a rotation of a first, second and third drive connector 118, 120, 122 of surgical device 100 into axial translation of drive tube 246 and drive bar 258 of adapter 200, to effectuate closing, opening, articulating and firing of end effector 300; or a rotation of ring gear 266 of adapter 200, to effectuate rotation of adapter 200.

As seen in FIGS. 13-19, first drive transmitting/converting assembly 240 includes a first distal drive shaft 242 rotatably supported within housing 202 and outer tube 206. A proximal end portion 242a of first distal drive shaft 242 is keyed to a spur gear 242c which is configured for connection to a spur gear 212a keyed to first rotatable proximal drive shaft 212, via a compound gear 243. First distal drive shaft 242 further includes a distal end portion 242b having a threaded outer profile or surface.

First drive transmitting/converting assembly 240 further includes a drive coupling nut 244 rotatably coupled to threaded distal end portion 242b of first distal drive shaft 242, and which is slidably disposed within outer tube 206. Drive coupling nut 244 is keyed to an inner housing tube 206a of outer tube 206 so as to be prevented from rotation as first distal drive shaft 242 is rotated. In this manner, as first distal drive shaft 242 is rotated, drive coupling nut 244 is translated through and/or along inner housing tube 206a of outer tube 206.

First drive transmitting/converting assembly 240 further includes a drive tube 246 surrounding first distal drive shaft 242 and having a proximal end portion connected to drive coupling nut 244 and a distal end portion extending beyond a distal end of first distal drive shaft 242. The distal end portion of drive tube 246 supports a connection member 247 (see FIG. 13) configured and dimensioned for selective engagement with drive member 374 of drive assembly 360 of end effector 300.

In operation, as first rotatable proximal drive shaft 212 is rotated, due to a rotation of first connector sleeve 218, as a result of the rotation of the first respective drive connector 118 of surgical device 100, spur gear 212a of first rotatable proximal drive shaft 212 engages first gear 243a of compound gear 243 causing compound gear 243 to rotate. As compound gear 243 rotates, a second gear 243b of compound gear 243 is rotated and thus causes spur gear 242c that is keyed to first distal drive shaft 242, that is engaged therewith, to also rotate thereby causing first distal drive shaft 242 to rotate. As first distal drive shaft 242 is rotated, drive coupling nut 244 is caused to be translated axially along first distal drive shaft 242.

As drive coupling nut 244 is caused to be translated axially along first distal drive shaft 242, drive tube 246 is caused to be translated axially relative to inner housing tube 206a of outer tube 206. As drive tube 246 is translated axially, with connection member 247 connected thereto and connected to a drive member 374 of drive assembly 360 of end effector 300, drive tube 246 causes concomitant axial translation of drive member 374 of end effector 300 to effectuate a closure of tool assembly 304 and a firing of tool assembly 304 of end effector 300.

With reference to FIGS. 13-19, second drive converter assembly 250 of adapter 200 includes second rotatable proximal drive shaft 214 rotatably supported within drive coupling assembly 210. Second rotatable proximal drive shaft 214 includes a non-circular or shaped proximal end portion 214a configured for connection with second connector 220 which is connected to respective second connector 120 of surgical device 100. Second rotatable proximal drive shaft 214 further includes a distal end portion 214b having a threaded outer profile or surface.

Figure 20:
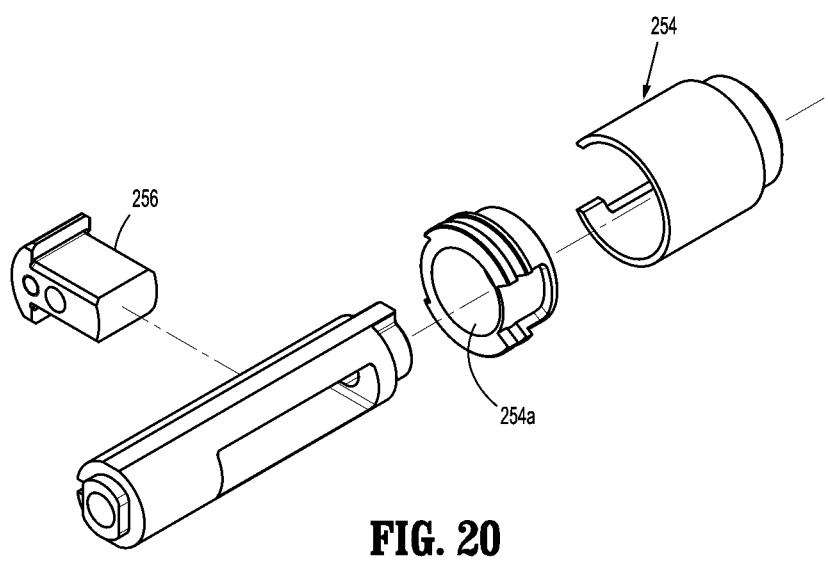
FIG. 20 is a perspective view, with parts separated, of a coupling cuff of the adapter of FIGS. 1 and 10.

As illustrated in FIG. 20, second drive converter assembly 250 further includes a coupling cuff 254 rotatably and translatably supported within an annular race or recess formed in knob housing 202. Coupling cuff 254 defines a lumen 254a therethrough, and an annular race or recess formed in a surface of lumen 254a. Second drive converter assembly 250 further includes a coupling slider 256 extending across lumen 254a of coupling cuff 254 and slidably disposed within the race of coupling cuff 254. Coupling slider 256 is threadably connected to threaded distal end portion 214b of second rotatable proximal drive shaft 214. As so configured, coupling cuff 254 can rotate about second rotatable proximal drive shaft 214, thereby maintaining a radial position of second rotatable proximal drive shaft 214 relative to first rotatable proximal drive shaft 242.

Second rotatable proximal drive shaft 214 defines an axis of rotation, and coupling cuff 254 defines an axis of rotation that is spaced a radial distance from the axis of rotation of second rotatable proximal drive shaft 214. Coupling slider 256 defines an axis of rotation that is coincident with the axis of rotation of coupling cuff 254.

Second drive converter assembly 250 further includes a drive bar 258 translatably supported for axial translation through outer tube 206. Drive bar 258 includes a proximal end portion 258a coupled to coupling cuff 254, and a distal end portion 258b defining a coupling hook 258c configured and dimensioned for selective engagement with hooked proximal end 366a of articulation link 366 of end effector 300. (see FIG. 21).

In operation, as illustrated in FIGS. 10-19, as drive shaft 214 is rotated due to a rotation of second connector sleeve 220, as a result of the rotation of the second drive connector 120 of surgical device 100, coupling slider 256 is caused to be translated axially along threaded distal portion 214b of second rotatable proximal drive shaft 214, which in turn causes coupling cuff 254 to be translated axially relative to knob housing 202. As coupling cuff 254 is translated axially, drive bar 258 is caused to be translated axially. Accordingly, as drive bar 258 is translated axially, with hook 258c thereof connected to hooked proximal end 366a of articulation link 366 of end effector 300 (see FIG. 21), drive bar 258 causes concomitant axial translation of articulation link 366 of end effector 300 to effectuate an articulation of tool assembly 304.

As seen in FIGS. 10-19 and as mentioned above, adapter 200 includes a third drive transmitting/converting assembly 260 supported in knob housing 202. Third drive transmitting/converting assembly 260 includes first and second rotation housing half-sections 262, 264 rotatably supported in knob housing 202, respectively, and an internal rotation ring gear 266 supported and interposed between first and second rotation housing half-sections 262, 264. Each of first and second rotation housing half-sections 262, 264 includes an arm 262a, 264b extending distally therefrom and which are parallel to one another and spaced a transverse distance from one another. Each arm 262a, 264a includes a boss 262b, 264b extending radially inward near a distal end thereof.

Third drive transmitting/converting assembly 260 further includes a pair of rotation transmitting bars 268, 270, each, connected at a proximal end thereof to bosses 262b, 264b of arms 262a, 264a, and at a distal end thereof to a distal coupling assembly 230 supported at a distal end of outer tube 206.

Third drive transmitting/converting assembly 260 includes a ring gear 266 defining an internal array of gear teeth 266a. Ring gear 266 includes a pair of diametrically opposed, radially extending protrusions 266b projecting form an outer edge thereof. Protrusions 266b are disposed within recesses 262c, 264c defined in an inner surface of first and second rotation housing half-sections 262, 264, such that rotation of ring gear 266 results in rotation of first and second rotation housing half-sections 262, 264.

Third drive transmitting/converting assembly 260 further includes third rotatable proximal drive shaft 216 rotatably supported within housing 202 and outer tube 206. A proximal end portion of third rotatable proximal drive shaft 216 is keyed to third connector 222 of adapter 200. Third rotatable proximal drive shaft 216 includes a spur gear 216a keyed to a distal end thereof. A gear set 274 inter-engages spur gear 216a of third rotatable proximal drive shaft 216 to gear teeth 266a of ring gear 266. Gear set 274 includes a first gear 274a engaged with spur gear 216a of third rotatable proximal drive shaft 216, and a second gear 274b engaged with gear teeth 266a of ring gear 266.

In operation, as illustrated in FIGS. 10-19, as third rotatable proximal drive shaft 216 is rotated, due to a rotation of third connector sleeve 222, as a result of the rotation of the third respective drive connector 122 of surgical device 100, spur gear 216a of third rotatable proximal drive shaft 216 engages first gear 272a of gear set 274 causing gear set 274 to rotate. As gear set 274 rotates, second gear 274b of gear set 274 is rotated and thus causes ring gear 266 to also rotate thereby causing first and second rotation housing half-sections 262, 264 to rotate. As first and second rotation housing half-sections 262, 264 are rotated, rotation transmitting bars 268, 270, and distal coupling assembly 230 connected thereto, are caused to be rotated about longitudinal axis "X" of adapter 200. As distal coupling 230 is rotated, end effector 300, that is connected to distal coupling assembly 230, is also caused to be rotated about a longitudinal axis of adapter 200.

With reference to FIGS. 10, 11, 13 and 18, adapter 200 further includes a lock mechanism 280 for fixing the axial position and radial orientation of drive tube 246 for the connection and disconnection of end effector 300 thereto. Lock mechanism 280 includes a button 282 slidably supported on knob housing 202. Lock button 282 is connected to an actuation bar 284 that extends longitudinally through outer tube 206. Actuation bar 284 is interposed between outer tube 206 and inner housing tube 206a. Actuation bar 284 moves upon a movement of lock button 282. Actuation bar 284 includes a distal portion 284a defining a window 284b therein. As seen in FIG. 18, a distal end of window 284b defines a cam surface 284c.

Figure 13:
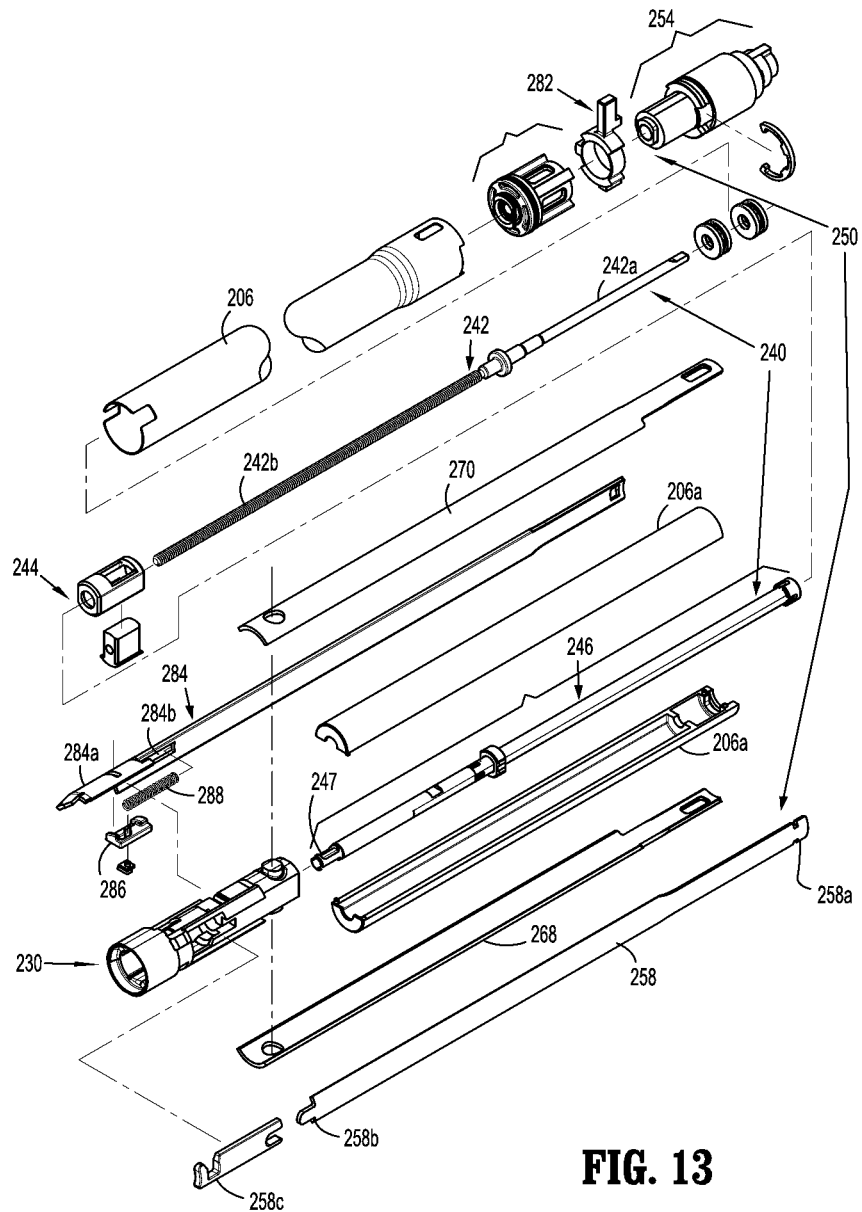
FIG. 13 is a perspective view, with parts separated, of a distal portion of the adapter of FIGS. 1 and 10.
Figure 14:
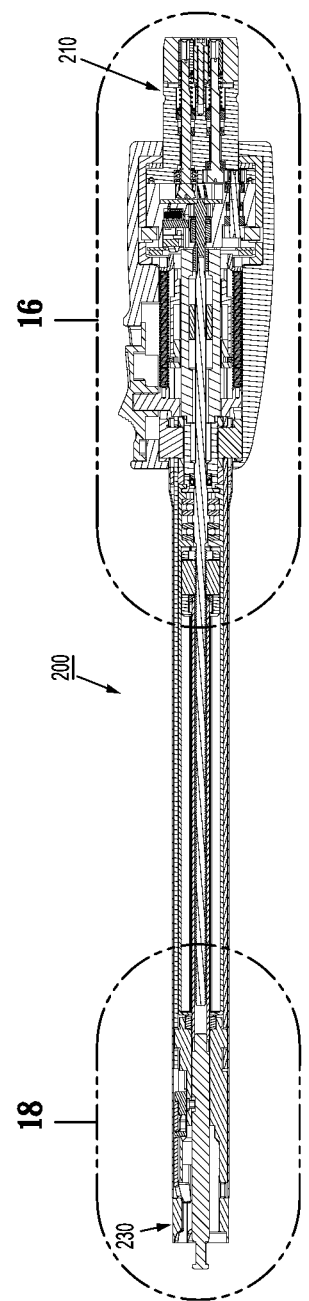
FIG. 14 is a cross-sectional view of the adapter of FIGS. 1 and 10, as taken through 14-14 of FIG. 10.
Figure 15:
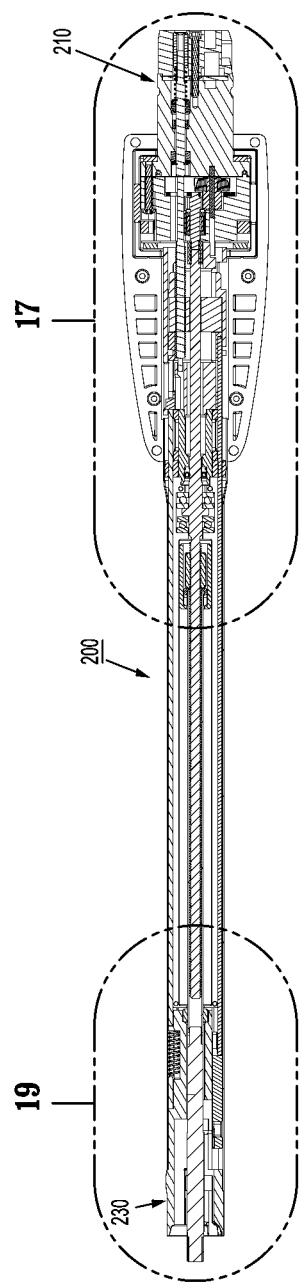
FIG. 15 is a cross-sectional view of the adapter of FIGS. 1 and 10, as taken through 15-15 of FIG. 10.
Figure 16:
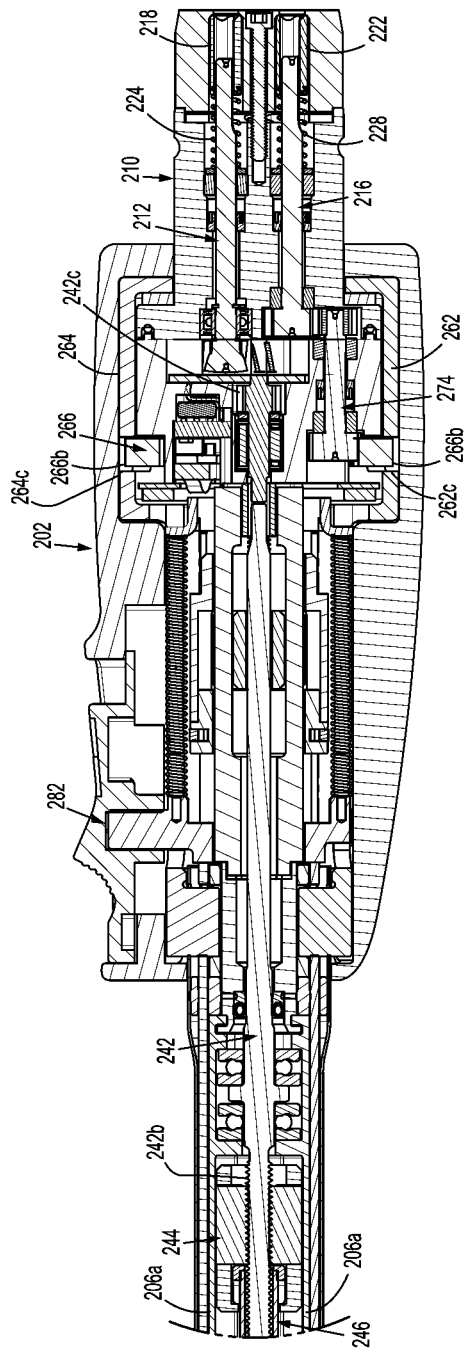
FIG. 16 is an enlarged view of the indicated area of detail of 14.
Figure 17:
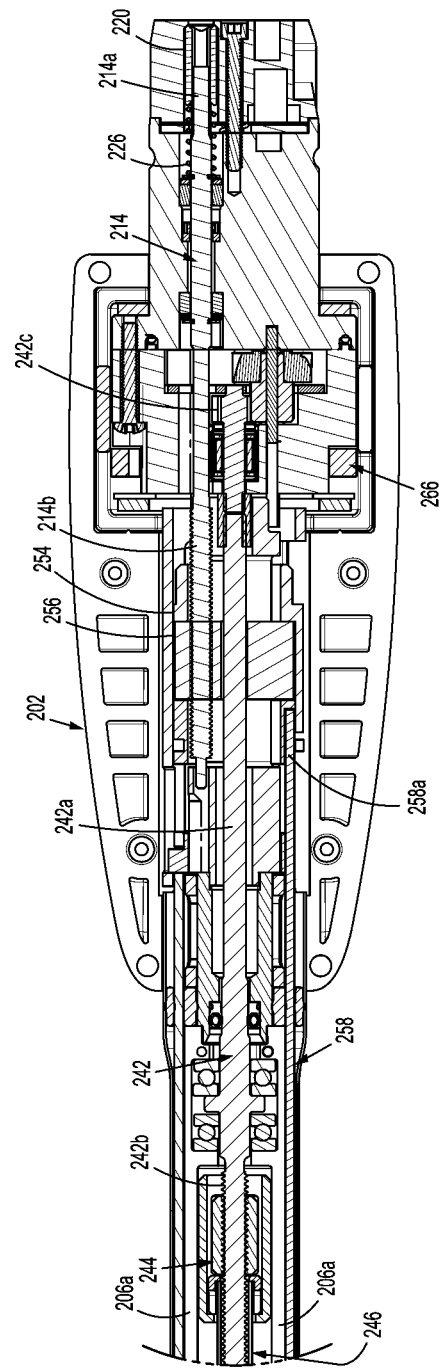
FIG. 17 is an enlarged view of the indicated area of detail of 15.

As illustrated in FIGS. 13 and 18, lock mechanism 280 further includes a lock out 286 supported on distal coupling assembly 230 at a location in registration with window 284b of distal portion 284a of actuation bar 284. Lock out 286 includes a tab 286a extending toward connection member 247 of drive tube 246. Tab 286a of lock out 286 is configured and dimensioned to selectively engage a cut-out 247a formed in connection member 247 of drive tube 246. Lock mechanism 280 further includes a biasing member 288 tending to maintain lock out 286 and tab 286a thereof spaced away from cut-out 247a formed in connection member 247 of drive tube 246.

In operation, in order to lock the position and/or orientation of drive tube 246, a user moves lock button 282 from a distal position to a proximal position, thereby causing cam surface 284c of actuation bar 284 to engage lock arm 286 and urge lock out 286 toward drive tube 246, against the bias of biasing member 288, such that tab 286a of lock out 286 is received in cut-out 247a formed in connection member 247 of drive tube 246.

In this manner, drive tube 246 is prevented from distal and/or proximal movement. When lock button 282 is moved from the proximal position to the distal position, cam surface 284c is disengaged from lock out 286 thereby allowing biasing member 288 to urge lock out 286 and tab 286a thereof out of cut-out 247a formed in connection member 247 of drive tube 246.

As seen in FIGS. 6 and 12, adapter 200 includes a pair of electrical contact pins 290a, 290b for electrical connection to a corresponding electrical plug 190a, 190b disposed in connecting portion 108a of surgical device 100. Electrical contacts 290a, 290b serve to allow for calibration and communication of necessary life-cycle information to circuit board 150 of surgical device 100 via electrical plugs 190a, 190b that are electrically connected to circuit board 150. Adapter 200 further includes a circuit board 292 supported in knob housing 202 and which is in electrical communication with electrical contact pins 290a, 290b.

When a button is activated by the user, the software checks predefined conditions. If conditions are met, the software controls the motors and delivers mechanical drive to the attached surgical stapler, which can then open, close, rotate, articulate or fire depending on the function of the pressed button. The software also provides feedback to the user by turning colored lights on or off in a defined manner to indicate the status of surgical device 100, adapter 200 and/or end effector 300.

A high level electrical architectural view of the system is displayed below in Schematic "A" and shows the connections to the various hardware and software interfaces. Inputs from presses of buttons 124, 126 and from motor encoders of the drive shaft are shown on the left side of Schematic "A". The microcontroller contains the device software that operates surgical device 100, adapter 200 and/or end effector 300. The microcontroller receives inputs from and sends outputs to a MicroLAN, an Ultra ID chip, a Battery ID chip, and Adaptor ID chips. The MicroLAN, the Ultra ID chip, the Battery ID chip, and the Adaptor ID chips control surgical device 100, adapter 200 and/or end effector 300 as follows:

MicroLAN—Serial 1-wire bus communication to read/write system component ID information.

Ultra ID chip—identifies surgical device 100 and records usage information.

Battery ID chip—identifies the Battery 156 and records usage information.

Adaptor ID chip—identifies the type of adapter 200, records the presence of an end effector 300, and records usage information.

Figure 22:
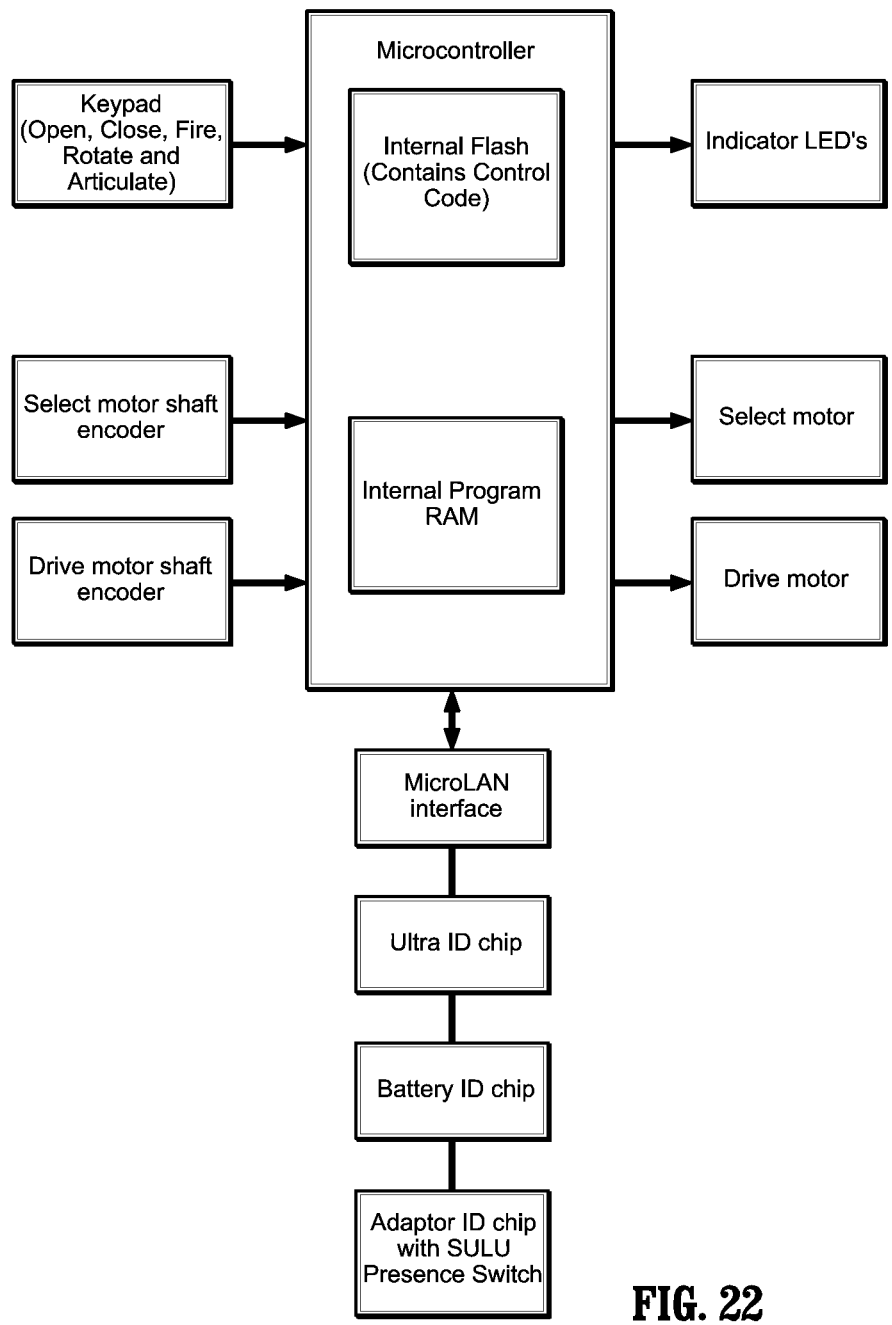
FIG. 22 is a schematic illustration of the outputs to the LED's; selection of motor (to select clamping/cutting, rotation or articulation); and selection of the drive motors to perform a function selected.

The right side of the schematic illustrated in FIG. 22 indicates outputs to the LED's; selection of motor (to select clamping/cutting, rotation or articulation); and selection of the drive motors to perform the function selected.

As illustrated in FIGS. 1 and 21, the end effector is designated as 300. End effector 300 is configured and dimensioned for endoscopic insertion through a cannula, trocar or the like. In particular, in the embodiment illustrated in FIGS. 1 and 21, end effector 300 may pass through a cannula or trocar when end effector 300 is in a closed condition.

End effector 300 includes a proximal body portion 302 and a tool assembly 304. Proximal body portion 302 is releasably attached to a distal coupling 230 of adapter 200 and tool assembly 304 is pivotally attached to a distal end of proximal body portion 302. Tool assembly 304 includes an anvil assembly 306 and a cartridge assembly 308. Cartridge assembly 308 is pivotal in relation to anvil assembly 306 and is movable between an open or unclamped position and a closed or clamped position for insertion through a cannula of a trocar.

Proximal body portion 302 includes at least a drive assembly 360 and an articulation link 366.

Referring to FIG. 21, drive assembly 360 includes a flexible drive beam 364 having a distal end which is secured to a dynamic clamping member 365, and a proximal engagement section 368. Engagement section 368 includes a stepped portion defining a shoulder 370. A proximal end of engagement section 368 includes diametrically opposed inwardly extending fingers 372. Fingers 372 engage a hollow drive member 374 to fixedly secure drive member 374 to the proximal end of beam 364. Drive member 374 defines a proximal porthole 376 which receives connection member 247 of drive tube 246 of first drive converter assembly 240 of adapter 200 when end effector 300 is attached to distal coupling 230 of adapter 200.

When drive assembly 360 is advanced distally within tool assembly 304, an upper beam of clamping member 365 moves within a channel defined between anvil plate 312 and anvil cover 310 and a lower beam moves over the exterior surface of carrier 316 to close tool assembly 304 and fire staples therefrom.

Proximal body portion 302 of end effector 300 includes an articulation link 366 having a hooked proximal end 366a which extends from a proximal end of end effector 300. Hooked proximal end 366a of articulation link 366 engages coupling hook 258c of drive bar 258 of adapter 200 when end effector 300 is secured to distal housing 232 of adapter 200. When drive bar 258 of adapter 200 is advanced or retracted as described above, articulation link 366 of end effector 300 is advanced or retracted within end effector 300 to pivot tool assembly 304 in relation to a distal end of proximal body portion 302.

As illustrated in FIG. 21, cartridge assembly 308 of tool assembly 304 includes a staple cartridge 305 supportable in carrier 316. Staple cartridge 305 defines a central longitudinal slot 305a, and three linear rows of staple retention slots 305b positioned on each side of longitudinal slot 305a. Each of staple retention slots 305b receives a single staple 307 and a portion of a staple pusher 309. During operation of surgical device 100, drive assembly 360 abuts an actuation sled and pushes actuation sled through cartridge 305. As the actuation sled moves through cartridge 305, cam wedges of the actuation sled sequentially engage staple pushers 309 to move staple pushers 309 vertically within staple retention slots 305b and sequentially eject a single staple 307 therefrom for formation against anvil plate 312.

Reference may be made to U.S. Patent Publication No. 2009/0314821, filed on Aug. 31, 2009, entitled "TOOL ASSEMBLY FOR A SURGICAL STAPLING DEVICE" for a detailed discussion of the construction and operation of end effector 300.

Since adapter 200 is reusable, prior to each use, at least adapter 200 must be sterilized using known sterilization techniques and methods (e.g., hand-washing, dishwashing and/or then autoclaving using cleaning fluids or the like). During this process, the cleaning fluids (e.g., water, detergent, etc.) may enter adapter 200, including inner housing tube 206a.

With reference to FIGS. 23 and 24, adapter 200 may be provided with an inner housing tube 206a including at least one, desirably a plurality of, port hole(s) or aperture(s) 206b formed therein. As seen in FIG. 23, an array of port holes 206b is formed in inner housing tube 206a, wherein the array is oriented to extend in a longitudinal direction along inner housing tube 206a. Desirably, an array of port holes 206b may be provided on diametrically opposed sides of inner housing tube 206a. Additionally, port holes 206b of the array may be evenly spaced relative to one another. While the array of port holes 206b has been shown including four (4) port holes 206b extending in a longitudinal direction, it is contemplated and within the scope of the present disclosure that inner housing tube 206a may be provided with an quantity, shape, size and arrangement of port holes or apertures 206b.

As so configured, any fluid that may have entered inner housing tube 206a, during the cleaning/sterilization process, has a path for egress. In particular, port holes 206b allow cleaning fluids to egress from inner housing tube 206a during or after the cleaning, dishwashing and/or autoclaving process. Additionally, during a drying period of the autoclaving process, the cleaning fluids can drain or evaporate out of inner housing tube 206a, via port holes 206b.

Turning now to FIGS. 25-30, adapter 200 may include a plurality of seals or the like which prevent the ingress of any fluids (e.g., cleaning fluids, bodily fluids, etc.) into inner housing tube 206a. As so constructed, any lubricants (e.g., grease) contained in the interior of inner housing tube 206a will remain therein during the cleaning/sterilization process.

Figure 27:
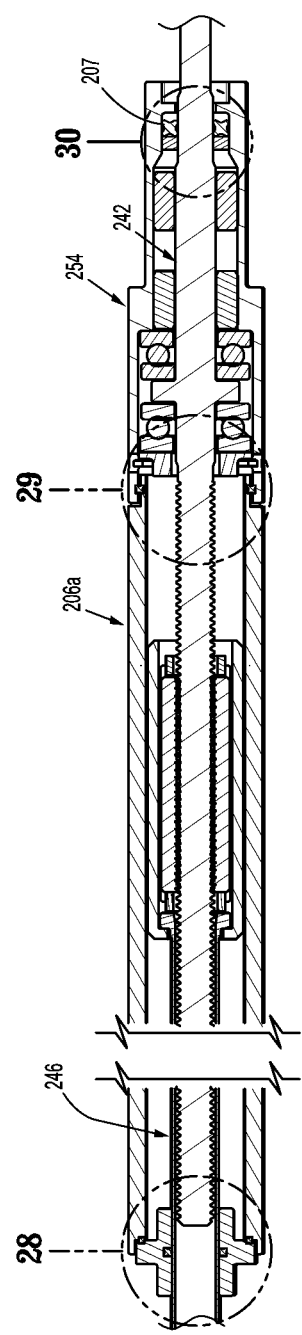
FIG. 27, is a longitudinal, cross-sectional view of the inner housing tube of FIGS. 25 and 26, as taken through 27-27 of FIG. 25.
Figure 28:
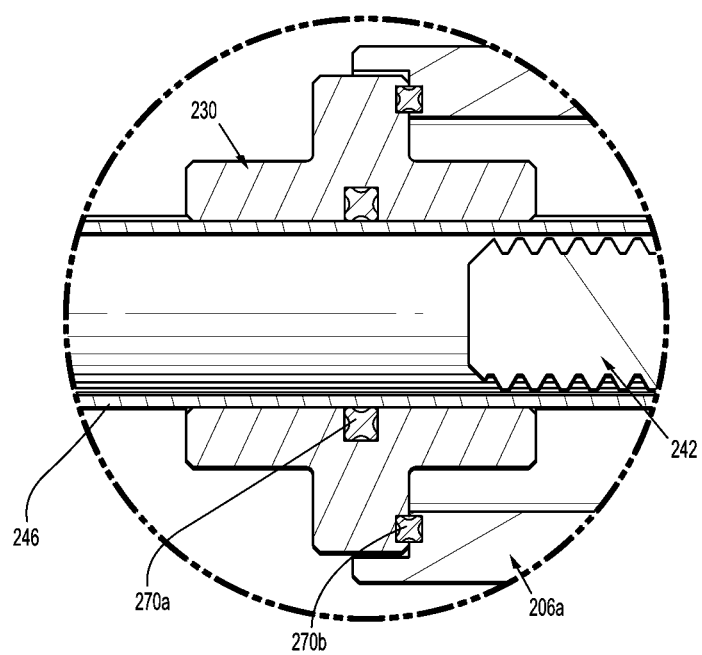
FIGS. 28-30 are enlarged views of the indicated areas of detail of FIG. 27.

In particular, as seen in FIGS. 27 and 28, adapter 200 may include a first seal 207a, in the form of a bi-directional seal (e.g., an X-ring gasket) interposed between distal coupling assembly 230 and drive tube 246. First seal 207a is configured to maintain pnuemostasis as well as to seal out fluids from entering inner housing tube 206a.

Adapter 200 may include a second seal 207b, in the form of a compression sleeve, and X-ring or the like, interposed between distal coupling assembly 230 and inner housing tube 206a. In addition or alternatively, a seal may be added interior to distal coupling assembly 230 and inner housing tube 206a and constrained therebetween.

Figure 29:
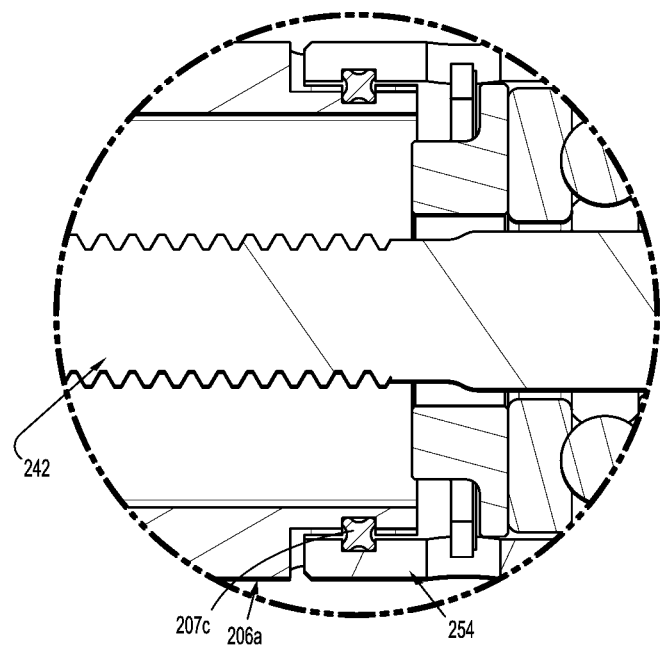

As seen in FIGS. 27 and 29, adapter 200 may also include a third seal 207c, in the form of an O-ring or X-ring gasket, recessed within a proximal bushing of adapter 200 to seal the interior features of inner housing tube 206a at a proximal end of inner housing tube 206a, wherein third seal 207c is interposed between an outer surface of inner housing tube 206a and an inner surface of coupling cuff 254.

Figure 30:
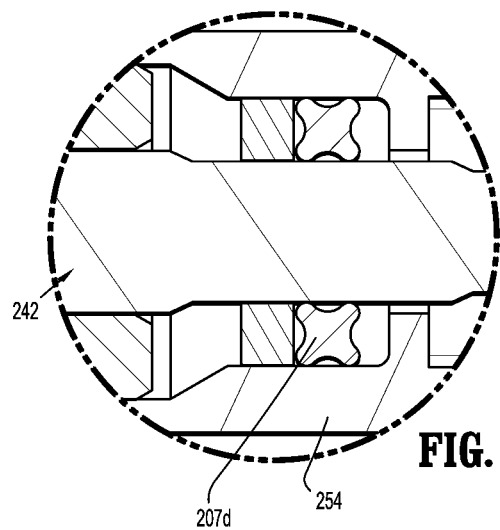

As seen in FIGS. 27 and 30, adapter 200 may also include a fourth seal 207d, in the form of an O-ring or X-ring gasket, recessed within an inner diameter of coupling cuff 254 of adapter 200 to ride on an outer diameter of first distal drive shaft 242.

Further, during the closing/opening and firing functions of surgical device 100 and end effector 300, as described above, first drive shaft 242 is rotated to axially displace drive coupling nut 244. During this process, heat can be generated due to the friction between drive coupling nut 244 and first drive shaft 242.

In this manner, inner housing tube 206a may include heat sinking or heat dissipation features in order to increase heat dissipation during the closing/opening and firing functions of surgical device 100 and end effector 300. The purpose of the heat sinking is to increase the surface area of inner housing tube 206a in order to dissipate heat more effectively.

In accordance with the present disclosure, heat can be dissipated from inner housing tube 206a by either conduction and convection.

Conduction takes place according to the following formula for the Rate of Heat Conduction:

$$Q_{cond} = k_t A \frac{\Delta T}{\Delta x};$$

where:
"$k_t$"=the thermal conductivity of the material, herein aluminum;
"A"=the surface area of the component, herein inner housing tube 206a; and $\frac{\Delta T}{\Delta x}$ = the temperature difference of the material across the thickness of the component, herein inner housing tube 206a.

Convection takes place according to the following formula for the Rate of Heat Convection:

$$Q_{conv} = hA(T_s - T_f); \text{ where:}$$

"h"=the convection heat transfer coefficient;
"A"=the surface area of the component, herein inner housing tube 206a;
"$T_s$"=the temperature of the surface of the component, herein inner housing tube 206a; and
"$T_f$"=the temperature of the fluid (e.g., air) surrounding the component, herein inner housing tube 206a.

Accordingly, by increasing a surface area of inner housing tube 206a, a rate of heat conduction and convection from inner housing tube 206a should increase. Thus, as seen in FIG. 31, inner housing tube 206a may be provided with a plurality of annular grooves 206c formed in an outer surface thereof and extending at least partially along a length thereof. While annular grooves are illustrated, as seen in FIG. 32, it is contemplated that longitudinally extending grooves 206d may also be formed in the outer surface of inner housing tube 206a to achieve the same or similar results. Grooves 206c, 206d may be of any quantity, shape, size and/or arrangement. Grooves 206c, 206d define ridges or ribs along the outer surface of inner housing tube 206a.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An adapter assembly for selectively interconnecting a surgical end effector that is configured to perform a function and a surgical device that is configured to actuate the end effector, the end effector including at least one axially translatable drive member, and the surgical device including at least one rotatable drive shaft, the adapter assembly comprising:
   a housing configured and adapted for connection with the surgical device and to be in operative communication with each of the at least one rotatable drive shaft of the surgical device;
   an inner housing tube having a proximal end supported by the housing, the inner housing tube defining an internal cavity and at least one aperture opening into the cavity;
   a distal coupling assembly disposed at a distal end of the inner housing tube, wherein the distal coupling assembly is configured to selectively connect with the end effector;
   at least one drive converter assembly for interconnecting a respective one of the at least one rotatable drive shaft of the surgical device and one of the at least one axially translatable drive member of the end effector, wherein the at least one drive converter assembly is at least partially disposed within the cavity of the inner housing tube, the at least one drive converter assembly including:
      a first end that is connectable to a first rotatable drive shaft of the surgical device; and
      a second end that is connectable to a first axially translatable drive member of the end effector, wherein the at least one drive converter assembly converts and transmits a rotation of the first rotatable drive shaft of the surgical device to an axial translation of the first axially translatable drive member of the end effector; and
   a plurality of seals disposed between the inner housing tube and the at least one drive converter assembly so as to prevent ingress of fluid into the cavity of the inner housing tube, wherein the plurality of seals includes a first seal interposed between the distal coupling assembly and a drive tube of the at least one drive converter assembly, the first seal being an X-ring gasket.

2. The adapter assembly according to claim 1, wherein the plurality of seals includes a second seal interposed between the distal coupling assembly and the inner housing tube.

3. The adapter assembly according to claim 2, wherein the second seal is a compression sleeve.

4. The adapter assembly according to claim 2, wherein the plurality of seals includes a third seal recessed within a proximal bushing of the adapter assembly.

5. The adapter assembly according to claim 4, wherein the third seal is one of an O-ring gasket and an X-ring gasket.

6. The adapter assembly according to claim 4, wherein the plurality of seals includes a fourth seal recessed within an inner diameter of the proximal bushing of adapter assembly to ride on an outer diameter of a first distal drive shaft of the at least one drive converter assembly.

7. The adapter assembly according to claim 6, wherein the fourth seal is one of an O-ring gasket and an X-ring gasket.

8. An adapter assembly for selectively interconnecting a surgical end effector that is configured to perform a function and a surgical device that is configured to actuate the end effector, the end effector including at least one axially translatable drive member, and the surgical device including at least one rotatable drive shaft, the adapter assembly comprising:
   a housing configured and adapted for connection with the surgical device and to be in operative communication with each of the at least one rotatable drive shaft of the surgical device;
   an inner housing tube having a proximal end supported by the housing, the inner housing tube defining an internal cavity and at least one aperture opening into the cavity;

a distal coupling assembly disposed at a distal end of the inner housing tube, wherein the distal coupling assembly is configured to selectively connect with the end effector;

at least one drive converter assembly for interconnecting a respective one of the at least one rotatable drive shaft of the surgical device and one of the at least one axially translatable drive member of the end effector, wherein the at least one drive converter assembly is at least partially disposed within the cavity of the inner housing tube, the at least one drive converter assembly including:

a first end that is connectable to a first rotatable drive shaft of the surgical device; and a second end that is connectable to a first axially translatable drive member of the end effector, wherein the at least one drive converter assembly converts and transmits a rotation of the first rotatable drive shaft of the surgical device to an axial translation of the first axially translatable drive member of the end effector; and a plurality of seals disposed between the inner housing tube and the at least one drive converter assembly so as to prevent ingress of fluid into the cavity of the inner housing tube, the plurality of seals including:

a first seal interposed between the distal coupling assembly and a drive tube of the at least one drive converter assembly; and a second seal interposed between the distal coupling assembly and the inner housing tube, the second seal being a compression sleeve.

* * * * *